US012807769B2

(12) United States Patent
Nelson et al.

(10) Patent No.: US 12,807,769 B2
(45) Date of Patent: Nov. 24, 2026

(54) HYDROGELS AND BIOPLASTICS INCLUDING GLOBULAR PROTEINS

(71) Applicant: University of Washington, Seattle, WA (US)

(72) Inventors: Alshakim Nelson, Seattle, WA (US); Patrick Thomas Smith, Seattle, WA (US); Siyami Cem Millik, Seattle, WA (US); Gokce Altin Yavuzarslan, Seattle, WA (US)

(73) Assignee: University of Washington, Seattle, WA (US)

( * ) Notice: Subject to any disclaimer, the term of this patent is extended or adjusted under 35 U.S.C. 154(b) by 898 days.

(21) Appl. No.: 18/076,369

(22) Filed: Dec. 6, 2022

(65) Prior Publication Data

US 2023/0174725 A1 Jun. 8, 2023

Related U.S. Application Data

(60) Provisional application No. 63/286,997, filed on Dec. 7, 2021.

(51) Int. Cl.
*C08J 3/075* (2006.01)
*A61L 27/16* (2006.01)
(Continued)

(52) U.S. Cl.
CPC ............... *C08J 3/075* (2013.01); *A61L 27/16* (2013.01); *A61L 27/227* (2013.01); *A61L 27/34* (2013.01); *A61L 27/52* (2013.01); *A61L 27/58* (2013.01); *A61L 31/047* (2013.01); *A61L 31/048* (2013.01); *A61L 31/10* (2013.01); *A61L 31/145* (2013.01); *A61L 31/148* (2013.01);
(Continued)

(58) Field of Classification Search
None
See application file for complete search history.

(56) References Cited

U.S. PATENT DOCUMENTS

| | | | | |
|---|---|---|---|---|
| 7,057,019 B2 * | 6/2006 | Pathak | .................. | A61K 47/42 530/380 |
| 7,183,040 B2 | 2/2007 | Thies | | |

(Continued)

FOREIGN PATENT DOCUMENTS

| | | | | |
|---|---|---|---|---|
| WO | WO-2020254206 A1 * | 12/2020 | ............. | C08L 23/12 |

OTHER PUBLICATIONS

Song et al. One-pot synthesis of soy protein (SP)-poly(acrylic acid) (PAA) superabsorbent hydrogels via facile preparation of SP macromonomer. Industrial Crops and Products. Jun. 2017, pp. 117-125, vol. 100. pp. 117-125 (Year: 2017).*

(Continued)

*Primary Examiner* — Sanza L. McClendon
(74) *Attorney, Agent, or Firm* — Katherine M. Mead; Lee & Hayes PC

(57) ABSTRACT

Hydrogels, bioplastics, and techniques for generating the same are described herein. An example method includes generating a resin including a globular protein, a co-monomer, water, and a photoinitiator. A hydrogel is generated by exposing the resin to light, thereby polymerizing the globular protein and the co-monomer. Further, the example method includes dehydrating the hydrogel by removing at least a portion of the water; and rehydrating the hydrogel in the presence of a hydrogen bonding agent.

19 Claims, 16 Drawing Sheets

(51) Int. Cl.
*A61L 27/22* (2006.01)
*A61L 27/34* (2006.01)
*A61L 27/52* (2006.01)
*A61L 27/58* (2006.01)
*A61L 31/04* (2006.01)
*A61L 31/10* (2006.01)
*A61L 31/14* (2006.01)
*C08J 3/24* (2006.01)

(52) U.S. Cl.
CPC ........... *C08J 3/245* (2013.01); *A61L 2420/00* (2013.01); *C08J 2335/02* (2013.01); *C08J 2351/08* (2013.01); *C08J 2389/00* (2013.01)

(56) References Cited

U.S. PATENT DOCUMENTS

| | | | | |
|---|---|---|---|---|
| 7,780,897 | B2 | 8/2010 | Wicker | |
| 12,180,374 | B2 * | 12/2024 | Nelson | C09D 11/30 |
| 2008/0095911 | A1 * | 4/2008 | Adams | A23L 33/20 426/573 |
| 2018/0297273 | A1 | 10/2018 | Rolland | |

OTHER PUBLICATIONS

Haddleton, D.M. et al. Protein-polymer bioconjugates via a versatile oxygen tolerant photoinduced controlled radical polymerization approach. Nat Commun 11, 1486 (2020). (Year: 2020).*
Theodorou et al. Oxygen tolerant, photoinduced controlled radical polymerization approach for the synthesis of giant amphiphiles. Polymer Chemistry, 2021, 12, 2228-2235 (Year: 2021) (Year: 2021).*
Ferracci et al. Photocurable Albumin Methacryloyl Hydrogels as a Versatile Platform for Tissue Engineering. ACS Applied Bio Materials. 2020, vol. 3, Issue 2, pp. 920-934. (Year: 2020).*
Abbate et al. Photocrosslinked bovine serum albumin hydrogels with partial retention of esterase activity. Enzyme and Microbial Technology. vol. 50(2); 2012, pp. 130-136 (Year: 2012).*
"Guide to Stereolithography," Formlabs, 2023, 23 pages.
"Tannic Acid—Molecule of the Week," American Chemical Society, Jan. 15, 2018, 4 pages.
Appuhamillage, et al., "110th Anniversary: Vat Photopolymerization-Based Additive Manufacturing: Current Trends and Future Directions in Materials Design," Ind. Eng. Chem. Res., vol. 58, 2019, pp. 15109-15118.
Bagheri and Jin, "Photopolymerization in 3D Printing," Appl. Polym. Mater., vol. 1, 2019, pp. 593-611.
CAS No. 9048-46-8, "Bovine Serum Albumin," Sigmna-Aldrich, Millipore Sigma, Accesssed online 2023 at https://www.sigmaaldrich.com/US/en/search/9048-46-8?focus=products&page=1&perpage=30&sort=relevance&term=9048-46-8&type=cas_number.
Chen and Hagerman, "Characterization of Soluble Non-covalent Complexes between Bovine Serum Albumin and B-1,2,3,4,6-Penta-O-galloyl-D-glucopyranose by MALDI-TOF MS," J. Agric. Food Chem., vol. 52, 2004, pp. 4008-4011.
Cheng, et al., "Enhanced adhesion and differentiation of human mesenchymal stem cell inside apatite-mineralized/poly (dopamine)-coated poly(e-caprolactone) scaffolds by stereolithography," J. Mater. Chem. B., 2016, 10 pages.
Da Silva, et al., "Assessing the Potential of Folded Globular Polyproteins As Hydrogel Building Blocks," Biomacromolecules, vol. 18, 2017, pp. 636-646.
Ding, et al., "Sustainable near UV-curable acrylates based on natural phenolics for stereolithography 3D printing," Polym. Chem., vol. 10, 2019, pp. 1067-1077.
Elomaa, et al., "Preparation of poly(e-caprolactone)-based tissue engineering scaffolds by stereolithography," Acta. Biomaterialia, vol. 7, 2011, pp. 3850-3856.
Fang, et al., "Forced protein unfolding leads to highly elastic and tough protein hydrogels," Nat. Comm., vol. 4, No. 2974, 2013, 10 pages.
Field, et al., "A Tuneable, Photocurable, Poly(Caprolactone)-Based Resin for Tissue Engineering Synthesis, Characterisation and Use in Stereolithography," Molecules, vol. 26, 2021, 21 pages.
Geyer, et al., "Production, use, and fate of all plastics ever made," Law Sci. Adv., vol. 3, 2017, 5 pages.
Giaveri, et al., "Nature-Inspired Circular-Economy Recycling for Proteins: Proof of Concept," Adv. Mater., vol. 33, 2021, 8 pages.
Gonzalez, et al., "Strong, Tough, Stretchable, and Self-Adhesive Hydrogels from Intrinsically Unstructured Proteins," Adv. Mater., vol. 29, 2017, 8 pages.
Han, et al., "Micro 3D Printing of a Temperature Responsive Hydrogel Using Projection Micro-Stereolithography," Nature, vol. 8, 2018, 10 pages.
Hernandez-Izquierdo and Krochta, "Thermoplastic Processing of Proteins for Film Formation—A Review," J. of Food Science, vol. 73, No. 2, 2008, 10 pages.
Hinczeski, et al., "Ceramic Suspensions Suitable for Stereolithography," J. European Ceramic Society, vol. 18, 1998, pp. 583-590.
Johari, et al., "Tuning the conformation and mechanical properties of silk fibroin hydrogels," European Polymer Journal, vol. 134, 2020, 15 pages.
Kapoor and Kundu, "Silk protein-based hydrogels: Promising advanced materials for biomedical applications," Acta. Biomaterialia., vol. 31, 2016, pp. 17-32.
Kim, et al., "Precisely printable and biocompatible silk fibroin bioink for digital light processing 3D printing," Nat. Commun., vol. 9, No. 16, 2018, 14 pages.
Labieniec and Gabryelak, "Interactions of tannic acid and its derivatives (ellagic and gallic acid) with calf thymus DNA and bovine serum albumin using spectroscopic method," J. Photochem. Photobiol., vol. 82, 2006, pp. 72-78.
Le Fer, et al., "Poly(propylene fumarate) stars, using architecture to reduce the viscosity of 3D printable resins," Polym. Chem., vol. 10, 2019, pp. 4655-4664.
Lee, et al., "Development of a tannic acid cross-linking process for obtaining 3D porous cell-laden collagen structure," J. Bio Macro., vol. 110, 2018, pp. 497-503.
Lim, et al., "Bio-resin for high resolution lithography-based biofabrication of complex cell-laden constructs," Biofabrication, vol. 10, 2018, 15 pages.
Lim, et al., "New Visible-Light Photoinitiating System for Improved Print Fidelity in Gelatin-Based Bioinks," ACS Biomater. Sc. Eng., vol. 2, 2016, pp. 1752-1762.
Lopes, et al., "Laser curing of silver-based conductive inks for in situ 3D structural electronics fabrication in stereolithography," J. Mat. Protec., vol. 214, 2014, pp. 1935-1945.
Lu, et al., "Probing the secondary structure of bovine serum albumin during heat-induced denaturation using mid-infrared fiberoptic sensors," Analyst, vol. 140, No. 3, 2015, pp. 673-946.
Luo, et al., "3D Printing of Poly(propylene fumarate) Oligomers: Evaluation of Resin Viscosity, Printing Characteristics and Mechanical Properties," Biomacromolecules, vol. 20, 2019, pp. 1699-1708.
Melchels, et al., "A review on stereolithography and its applications in biomedical engineering," Biomaterials, vol. 31, 2010, pp. 6121-6130.
Mohammed, et al., "Polysaccharides, Protein and Lipid-Based Natural Edible Films in Food Packaging: A Review," Carbohydrate Polymers, vol. 238, 2020, 14 pages.
Mondschein, et al., "Polymer structure-property requirements for stereolithographic 3D printing of soft tissue engineering scaffolds," Biomaterials, vol. 140, 2017, pp. 170-188.
Murr, et al., "Frontiers of 3D Printing/Additive Manufacturing: from Human Organs to Aircraft Fabrication," JMST, vol. 32, 2016, pp. 987-995.
Nakahata, et al., "Highly Flexible, Tough, and Self-Healing Supramolecular Polymeric Materials Using Host Guest Interaction," Macromol. Rapid. Commun., vol. 37, 2016, pp. 86-92.
Nelson, Alshakim, "In Situ Production and Continuous Delivery of Therapeutics by 3D-Printed Engineered Living Materials," University of Washington, 2022, 13 pages.

(56) References Cited

OTHER PUBLICATIONS

Nonoyama, et al., "Tough Double Network Hydrogel and Its Biomedical Applications," Annu. Rev. Chem. Biomol., vol. 12, 2021, pp. 393-410.
O'Dea, et al., "100th Anniversary of Macromolecular Science Viewpoint: Polymers from Lignocellulosic Biomass. Current Challenges and Future Opportunities," ACS Macro. Lett., vol. 9, 2020, pp. 476-493.
Osawa and Walsh, "Effects of Acidic and Alkaline Treatments on Tannic Acid and Its Binding Property to Protein," J. Agric. Food Chem., vol. 41, 1993, pp. 704-707.
Peak, et al., "A review on tough and sticky hydrogels," Colloid Polym Sci., vol. 291, 2013, pp. 2031-2047.
Pirsa, et al., "A review of the applications of bioproteins in the preparation of biodegradable films and polymers," J. Chem. Lett., vol. 1, 2020, pp. 47-58.
Poldervaart, et al., "3D bioprinting of methacrylated hyaluronic acid (MeHA) hydrogel with intrinsic osteogenicity," PLOS ONE, vol. 12, No. 6, 2017, 15 pages.
Quideau, et al., "Plant Polyphenols: Chemical Properties, Biological Activities, and Synthesis," Angew. Chem. Int. Ed., vol. 50, 2011, pp. 586-621.
Sanchez-Rexach, et al., "3D-Printed Bioplastics with Shape-Memory Behavior Based on Native Bovine Serum Albumin," ACS Appl. Mater. Interfaces, vol. 13, 2021, pp. 19193-191999.
Sanchez-Rexach, et al., "Sustainable Materials and Chemical Processes for Additive Manufacturing," Chem. Mater., vol. 32, 2020, pp. 7105-7119.
Schneiderman, et al., "50th Anniversary Perspective: There Is a Great Future in Sustainable Polymers," Macromolecules, vol. 50, 2017, pp. 3733-3748.
Schuller-Ravoo, et al., "Flexible and Elastic Scaffolds for Cartilage Tissue Engineering Prepared by Stereolithography Using Poly(trimethylene carbonate)-Based Resins," Macromol. Biosci., vol. 13, 2013, pp. 1711-1719.
Seiler, Matthias, "Hyperbranched polymers: Phase behavior and new applications in the field of chemical engineering," Fluid phase Equilibria, vol. 241, 2006, pp. 155-174.
Shanmugam and Polavarapu, "Vibrational circular dichroism spectra of protein films: thermal denaturation of bovine serum albumin," Biophysical Chemistry, vol. 111, 2004, pp. 73-77.
Smith, et al., "Additive Manufacturing of Bovine Serum Albumin-Based Hydrogels and Bioplastics," Biomacromolecules, vol. 21, 2020, pp. 484-492.
Smith, et al., "Methacrylated Bovine Serum Albumin and Tannic Acid Composite Materials for Three-Dimensional Printing Tough and Mechanically Functional Parts," ACS Appl. Mater. Intrerfaces, vol. 14, 2022, pp. 21418-21425.
Sun, et al., "Molecular engineering of metal coordination interactions for strong, tough, and fast-recovery hydrogels," Sci. Adv., vol. 6, 2020, 12 pages.
Sutton, et al., "Lignin-Containing Photoactive Resins for 3D Printing by Stereolithography," ACS Appl. Mater. Interfaces, vol. 10, 2018, pp. 36456-3646.
Tagliazucchi, et al., "Effect of Some Phenolic Compounds and Beverages on Pepsin Activity during Simulated Gastric Digestion," J. Agric. Food Chem., vol. 53, 2005, pp. 8706-8713.
"Chemisrty of Crosslinking," Thermo Fisher Scientific, 2013, 11 pages.
Tumbleston, et al., "Continuous liquid interface production of 3D objects," Science, vol. 347, No. 6228, 2015, pp. 1349-1352.
Voit and Lederer, "Hyperbranched and Highly Branched Polymer Architecturess Synthetic Strategies and Major Characterization Aspects," Chem. Rev., vol. 109, 2009, pp. 5924-5973.
Walker, et al., "Rapid, large-volume thermally controlled 3D printing using a mobile liquid interface," Science, vol. 366, 2019, pp. 360-364.
"Bovine Serum Albumin," Wikipedia, retreived from https://en.wikipedia.org/w/index.php?title=Bovine_serum_albumin&oldid=1124814350.
Xing, et al., "Increasing Mechanical Strength of Gelatin Hydrogels by Divalent Metal lon Removal," Scientific Reports, vol. 4, No. 4706, 2014, 10 pages.
Yin, et al., "3D Bioprinting of Low-Concentration Cell-Laden Gelatin Methacrylate (GelMA) Bioinks with a Two-Step Cross-linking Strategy," ACS Appl. Mater. Interfaces., vol. 10, 2018, pp. 6849-6857.
Zhang, et al., "Inspired by elastomers: fabrication of hydrogels with tunable properties and re-shaping ability via photo-crosslinking at a macromolecular level," Poly. Chem., vol. 8, 2017, pp. 1824-1832.
Zhao, et al., "Engineering Nonmechanical Protein-Based Hydrogels with Highly Mechanical Properties: Comparison with Natural Muscles," Biomacromolecules, vol. 21, 2020, pp. 4212-4219.
Zhao, et al., "Soft Materials by Design: Unconventional Polymer Networks Give Extreme Properties," Chem. Rev., vol. 121, 2021, pp. 4309-4372.
Zhao, Xuanhe, "Multi-scale multi-mechanism design of tough hydrogels: building dissipation into stretchy networks," Soft. Matter., vol. 10, 2014, pp. 672-687.
Zheng, et al., "Metal-Coordination Complexes Mediated Physical Hydrogels with High Toughness, Stick-Slip Tearing Behavior, and Good Processability," Macromolecules, vol. 49, 2016, pp. 9637-9646.
Zhou, et al., "Engineering hydrogels by soaking: from mechanical strengthening to environmental adaptation," Chem. Commun., vol. 56, 2020, 17 pages.
Zuev, et al., "3D Printing and Bioprinting using Multiphoton Lithography," Bioprinting, vol. 20, No. 7-8, 2020, 34 pages.

* cited by examiner

Tannic Acid
(TA)

HYDROGELS AND BIOPLASTICS INCLUDING GLOBULAR PROTEINS

CROSS-REFERENCE TO RELATED APPLICATION

This application claims the benefit of U.S. Provisional Application No. 63/286,997, filed on Dec. 7, 2021, and which is incorporated by reference herein in its entirety.

BACKGROUND

The growing use of plastics and rapid accumulation of plastic waste calls for the development of alternative materials that are promptly degradable and environmentally benign. Proteins represent a class of biopolymers with remarkable structural and functional diversity. Utilizing proteins for commercial materials applications can reduce reliance on petroleum-based materials, as protein feedstocks can be obtained in high volumes from microbial, plant, and animal sources. Silk fibroin, collagen, gelatin, and bovine serum albumin (BSA) are examples of proteins and protein derivatives that have thus far been investigated for materials applications that range from commodity materials to specialized biomedical materials. Protein-based materials can generally be processed via solvent casting, melt extrusion, and injection molding. However, for biopolymers formed from protein monomers, deposition of the biopolymer is limited by poor processability to create three dimensional (3D) shapes. Additionally, the biopolymers formed from the protein monomers are commonly characterized by poor mechanical performance.

Vat photopolymerization 3D printing techniques such as stereolithographic apparatus (SLA) 3D printing, digital light processing (DLP), continuous liquid interface production (CLIP), and high-area rapid printing (HARP) have emerged as promising techniques that offer high quality parts at increasingly fast production rates. The list of 3D printable elastomers, plastics, and composites reported in the literature continues to grow; however, most of these materials are not biodegradable, and only a few are based on biopolymers. The design of photocurable resins for vat photopolymerization requires photo-crosslinkable molecules with low intrinsic viscosities and fast photocuring rates. In general, a low resin viscosity (0.25 Pa·s to 10 Pa·s) is used to facilitate resin reflow and minimize the undesirable stresses exerted on the printed object during the printing process. Increasing the polymer concentration in the resin increases viscosity, as does increasing the molecular weights of the polymeric components, as predicted by Mark-Houwink equation. An alternative design strategy is to employ synthetic polymers with cyclic, branched, or dendritic architectures, or cross-linked unimolecular particles. These architectures are characterized by low intrinsic viscosities relative to that of a linear polymer counterpart. Notably, the majority of photocurable protein derivatives that have thus far been reported are based on structural proteins (e.g., gelatin and silk fibroin), which form fibrous higher-order assemblies. The use of these anisotropic structures is counterproductive in vat photopolymerization processes, as this substantially increases the resin viscosity, which can limit processability.

Currently, and as noted above, the commercial resins for vat photopolymerization processes lack the ability to be biodegraded for disposal. Additionally, polymers with the capability to be biodegraded commonly lack sufficient mechanical strength and/or mechanical performance.

SUMMARY OF THE DISCLOSURE

The present disclosure provides systems and methods for deposition of a biopolymer and subsequent treatment of the biopolymer to improve the mechanical performance such that a biodegradable biopolymer that can be printed into various 3D shapes via photopolymerization processes.

Nature can manipulate and pattern proteins into complex 3D architectures that include spiderwebs and tissue, and these biomaterials have mechanical properties that are challenging to replicate in synthetic systems. Moreover, all of these biomaterials are recycled or biodegraded within a closed-loop. In the absence of biological machinery, synthetic protein-based materials can be difficult to process and can have a limited range of mechanical properties. Herein, a multi-step additive manufacturing workflow to fabricate tough, protein-based composite hydrogels and bioplastics with a range of mechanical properties is described. First, methacrylated bovine serum albumin (MABSA)-based aqueous resins were 3D printed using a commercial stereolithographic apparatus (SLA) 3D printer. Next, the materials were treated with tannic acid (TA) to introduce additional noncovalent interactions within the network to improve mechanical properties. In the last step, a denaturing 120° C. thermal cure served to further enhance mechanical properties via formation of intermolecular β-sheets and other noncovalent interactions. The combination of TA treatment and thermal cure virtually eliminated rehydration of the materials, enabling application as bioplastics. Compression and tensile studies of 3D printed constructs demonstrated a range of ultimate strengths, elastic moduli and toughness that could be modulated by adjusting resin composition and post-print treatment protocol. 3D printed hydrogels enzymatically degraded up to 85% after 30 days in pepsin solution. To highlight the diverse mechanical functionality achievable with these materials, a bioplastic screw was 3D printed and driven into wood without damage to the screw. Finally, the hydrogel material could be sutured, and the suture could be placed under mechanical load without signs of failure even after immersion in water for 24 h.

C. thermal cure denatured the MABSA and reduced rehydration to form a dMABSA-TA bioplastic.

Figure 9A:
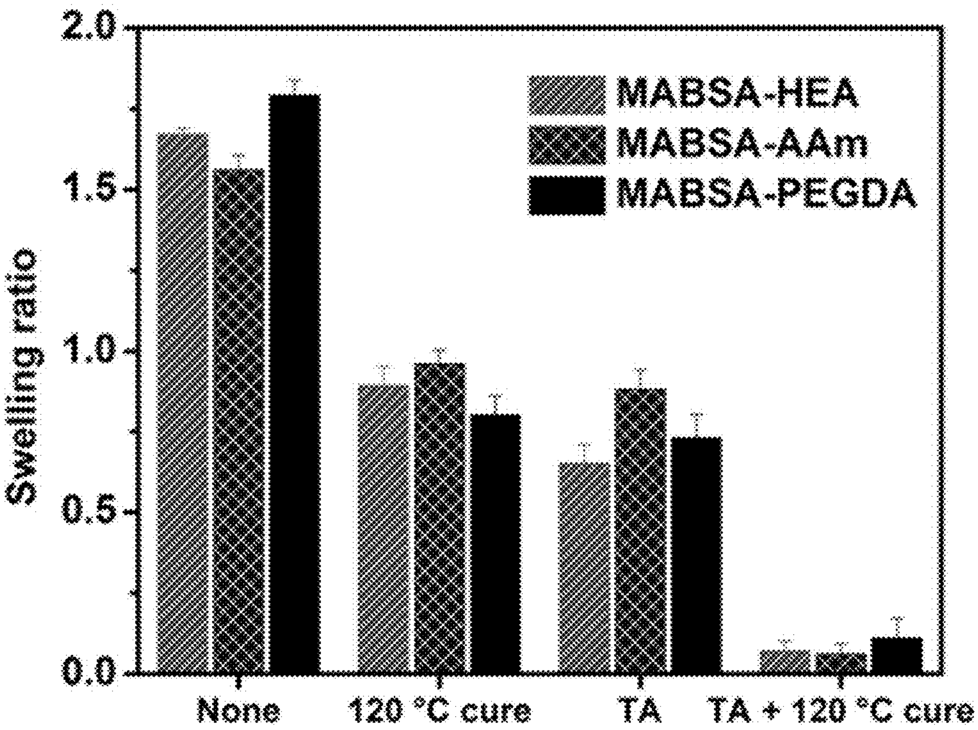
Figure 9B:
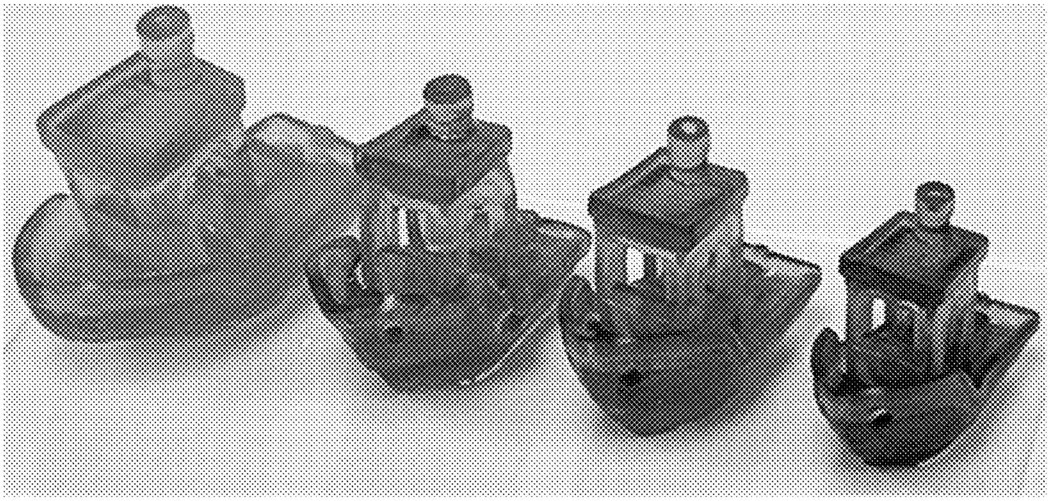

FIGS. 9A and 9B illustrate (9A) a swelling ratio of 3D printed MABSA-based formulations after each post-print treatment including no treatment, 120° C. thermal cure, TA treatment, and TA treatment and 120° C. thermal cure and (9B) printed MABSA-hydroxyethylacrylate (HEA) shapes at equilibrium swelling in DI water after each post-print treatment: none, 120° C. thermal cure, TA treatment, and TA treatment and thermal cure (from left to right).

FIGS. 10A-10J illustrate (10A-C) tensile stress-strain curves of all formulations at equilibrium swelling (10A) with no post-print treatment, (10B) after TA treatment, (10C) after TA treatment and 120° C. thermal cure. (10D) Young's modulus, (10E) toughness, and (10F) Ultimate strength of each formulation with no post-print treatment, 120° C. thermal cure, TA treatment, and both TA treatment and 120° C. thermal cure. (10G) 3D printed bioplastic screw after TA treatment and 120° C. thermal cure. (10H) Bioplastic screw being driven into wood. (i) Side view of bioplastic screw in wood, (10J) Bioplastic screw after removal from wood, lacking visible damage.

FIGS. 11A-11F illustrate degradation of printed constructs over 30 d in pepsin solution (11A) MABSA-HEA, (11B) MABSA-acrylamide (AAm), (11C) MABSA-poly (ethylene glycol) diacrylate (PEGDA). Images of MABSA-HEA, MABSA-HEA-TA, dMABSA-HEA, and dMABSA-HEA-TA at (11D) day 0 prior to incubation in pepsin solution, (11E) after 5 d incubation in pepsin solution, (11F) after 30 d incubation in pepsin solution.

FIGS. 12A-12G illustrate the suturability of MABSA-HEA hydrogels. The suturing of a 3D printed hydrogel (12A) with no post-print treatment (MABSA-HEA hydrogel) and (12B) after TA treatment (MABSA-HEA-TA hydrogel). (12C) MABSA-HEA-TA hydrogel supporting a 500 g weight via a single suture. (12D, 12E) MABSA-HEA-TA hydrogel patch sutured to bovine small intestine; front and back views respectively. (12F, 12G) MABSA-HEA-TA patch sutured to bovine small intestine after 24 hours immersed in water.

Figure 13:
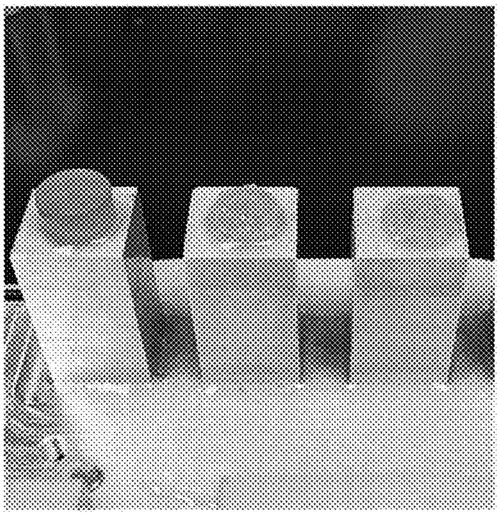

FIG. 13 illustrates the printability of tested resin formulations. 1 wt % AAm, 2 wt % AAm, and 3 wt % AAm (left to right).

Figure 14A:
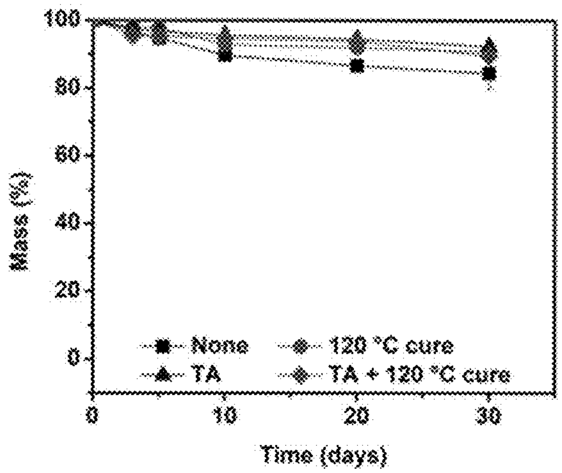
Figure 14B:
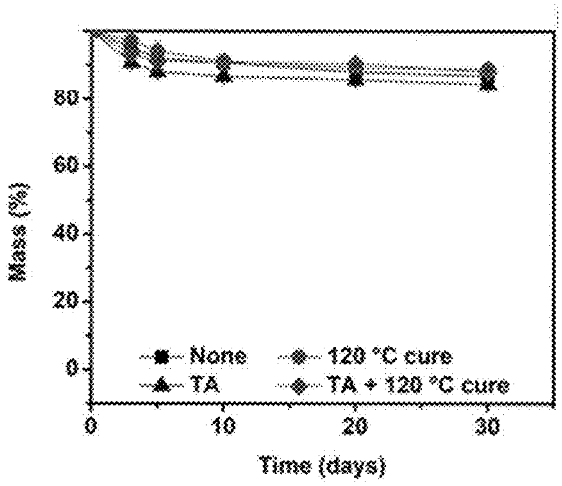
Figure 14C:
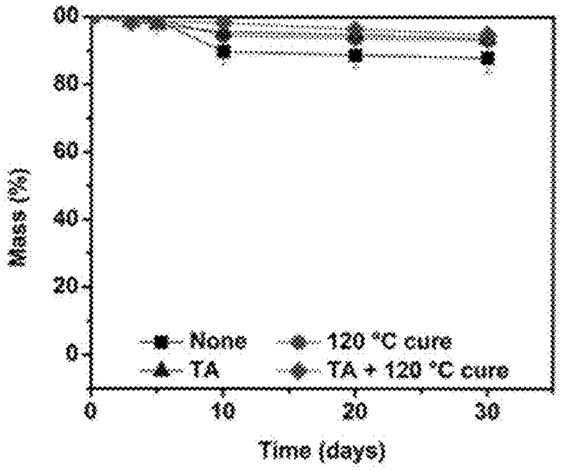

FIGS. 14A to 14C illustrates the mass percent degradation over 30 days in DI water for HEA (14A), AAm (14B), and PEGDA (14C) based biopolymers, respectively.

Figure 15A:
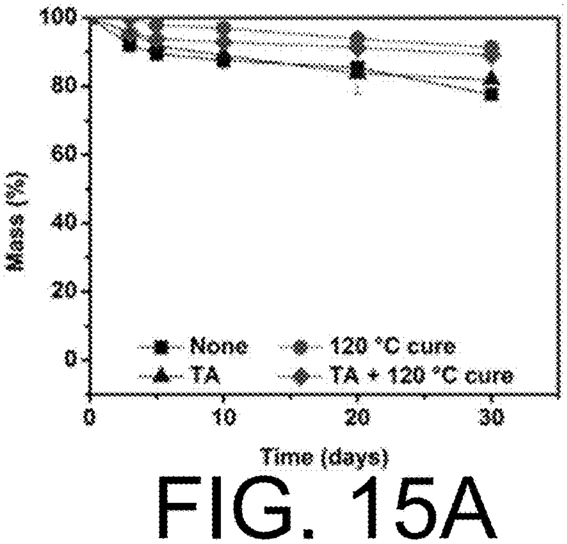
Figure 15B:
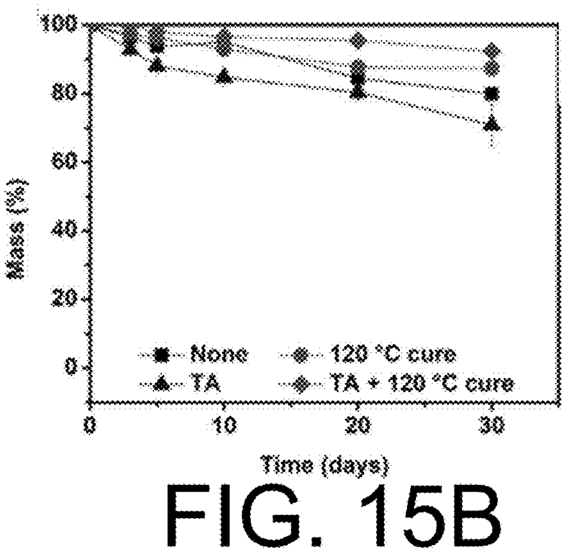
Figure 15C:
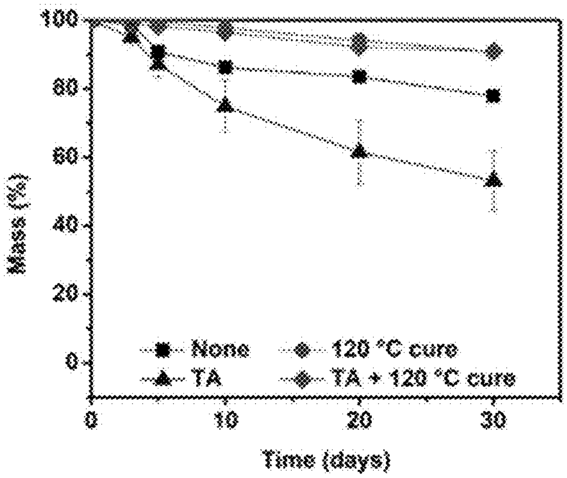

FIGS. 15A to 15C illustrates the mass percent degradation over 30 days in HCl solution for HEA (15A), AAm (15B), and PEGDA (15C) based biopolymers, respectively.

Figure 16:
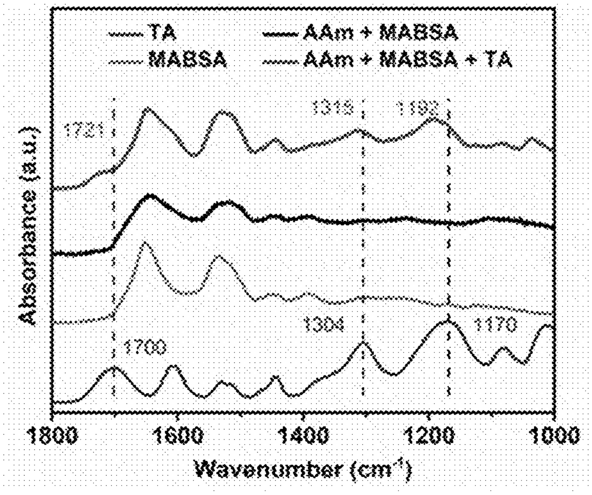

FIG. 16 illustrates ATR-FTIR spectra of TA, MABSA, MABSA-AAm, and MABSA-AAm-TA.

Figure 17:
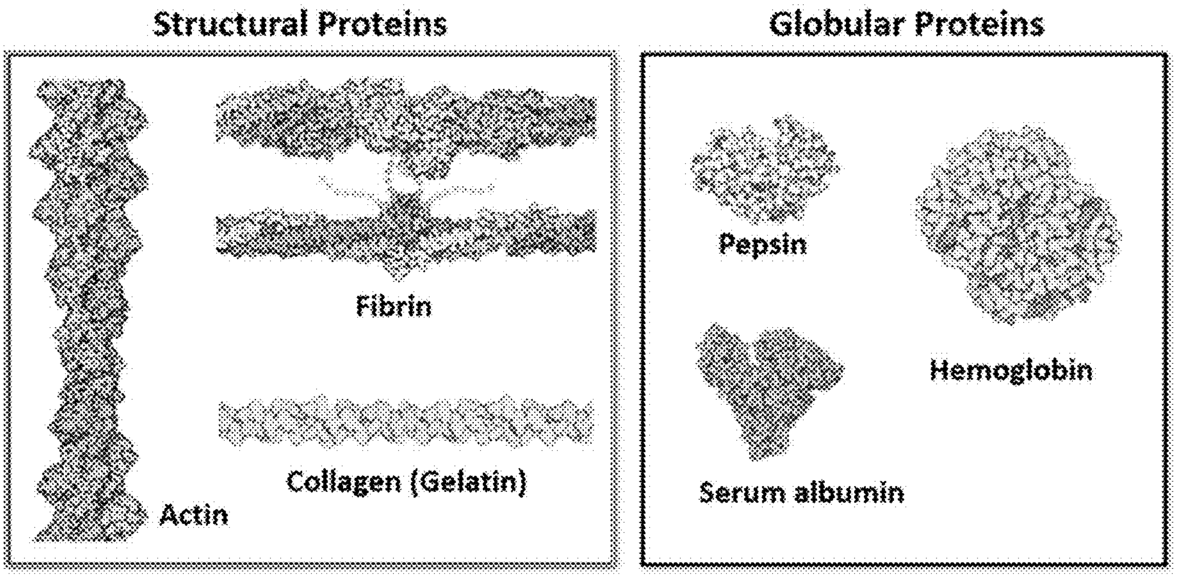

FIG. 17 illustrates globular protein structures that may be utilized for formation of hydrogels and bioplastics for photopolymerization and 3D printing.

Figure 18:
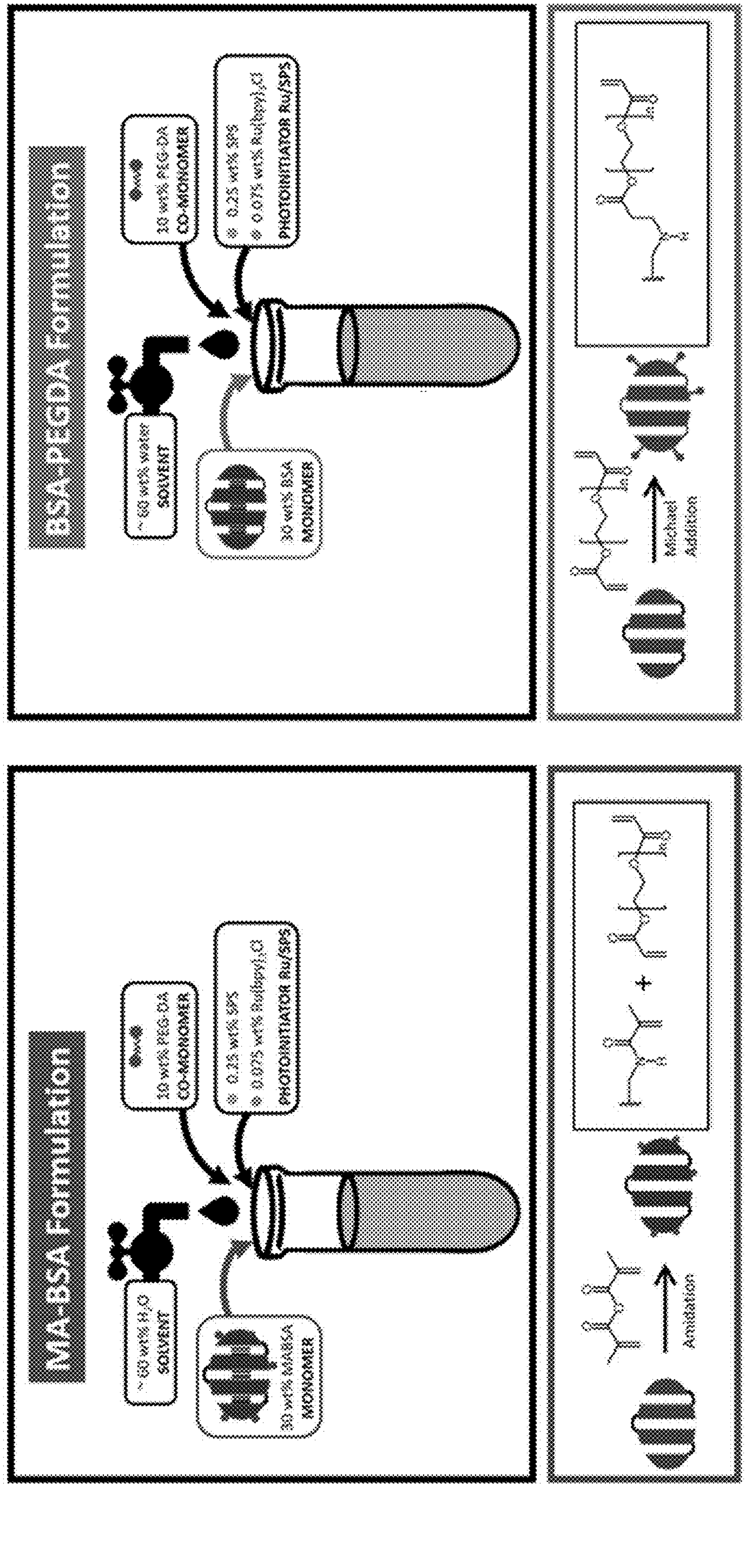

FIG. 18 illustrates example resin formulations according to various implementations described herein.

DETAILED DESCRIPTION

Implementations of the present disclosure provide systems and methods for fabricating biodegradable 3D constructs from a biopolymer material, which can be utilized as a tough hydrogel or dehydrated bioplastic. In particular, the biopolymer can be deposited via resin formulations and SLA 3D printing processes. The resin formulations described herein commonly include a methacrylated globular protein (e.g., methacrylated bovine serum albumin (MABSA)) and water-soluble acrylate monomers. A hydrogel construct, for example, is generated by crosslinking the components of the resin formulations.

The mechanical properties of example hydrogel constructs can be enhanced with the incorporation of a polyphenol agent (e.g., tannic acid (TA)) into the crosslinked MABSA network. As shown in various experimental examples described herein, MABSA-TA composite hydrogels exhibit increased toughness when compared to the MABSA hydrogels that were printed without incorporation of TA. The incorporation of TA enables the formation of secondary noncovalent crosslinks within the MABSA network.

In some implementations, hydrogel constructs are converted to bioplastic constructs. For example, the MABSA-TA composites can be thermally cured (e.g., at 120° C.) to unfold α-helical regions and concomitantly form β-sheet structures, thereby enhancing mechanical properties. Thermally denatured MABSA-TA (dMABSA-TA) composites are examples of bioplastics. The presence of TA in these bioplastics enhanced mechanical properties and prevented rehydration of these materials when immersed in water. The improvements in material strength, elastic modulus, and toughness for these protein-based materials enables 3D printed constructs to be formed that remain mechanically functional, such as screws and suturable substrates.

Bovine serum albumin (BSA) is a globular protein that is well suited for vat photopolymerization 3D printing. At around neutral pH (e.g., a pH of 6-8), BSA exhibits high aqueous solubility (up to 50 wt %) largely due to its high surface charge. Additionally, BSA has a low intrinsic viscosity, which is related to its compact nanoparticle-like structure. Together, the high solubility and low intrinsic viscosity of BSA facilitate high BSA loading into resins as well as facile processing of BSA-based resins. Methacrylated BSA (MABSA) was synthesized by functionalizing available surface lysines of BSA. Unlike gelatin methacrylate (GelMA), MABSA does not naturally form physical hydrogels at moderate concentrations (2-40 wt %) in water. This photo-crosslinkable derivative of BSA can be utilized to prepare resins for vat photopolymerization 3D printing using a commercially available 3D printer. While a mechanically stiff (6 MPa) hydrogels were reported, the applicability of this material for a broader array of load-bearing applications was limited by its swelling in water, which reduced its mechanical strength. Additionally, poly(ethylene glycol) diacrylate (PEGDA) was utilized for network formation but also provides resistance to complete enzymatic degradation of the BSA-PEGDA material.

It should be noted that while BSA is the protein discussed as the primary example for the methods described herein, similar methods and/or processes can be utilized with other proteins. In particular, other globular proteins may be utilized in place of BSA due to the globular proteins being soluble in aqueous solution while experiencing minimal changes in solution viscosity with increasing concentrations. Additionally, while the BSA is converted into MABSA, other proteins can be similarly methacrylated via lysines that are exposed on the outer surface of the globular protein. For example, pepsin, hemoglobin, lysozyme, lactoglobulin, whey, and soy protein are other globular proteins that may be utilized to form the hydrogels and the bioplastics described herein.

TA is a plant-sourced polyphenol that has been shown to enhance the mechanical properties of synthetic and biopolymer hydrogels. TA can introduce secondary crosslinks within polymeric networks through hydrogen bonding and hydrophobic interactions to enhance the elastic modulus, strength, and toughness of a hydrogel. Additionally, the noncovalent interactions with TA can reduce the extent of swelling of a polymer network and provide sacrificial bonds as an energy dissipation mechanism that improves mechanical toughness.

It should be noted that while TA is the toughening agent described for the methods and the hydrogels described herein, other toughening agents may be utilized. In particular, TA is utilize due to the large molecular structure and the plurality of hydrogen bonding sites within the molecule. Accordingly, other toughening agents may be utilized that include a plurality of hydrogen bonding cited capable of crosslinking the globular proteins and the comonomers of the biopolymers. Further, the toughening agent may be chosen as a large molecule similar to tannic acid or a smaller molecule that includes the plurality of hydrogen bonding sites.

Figure 1:
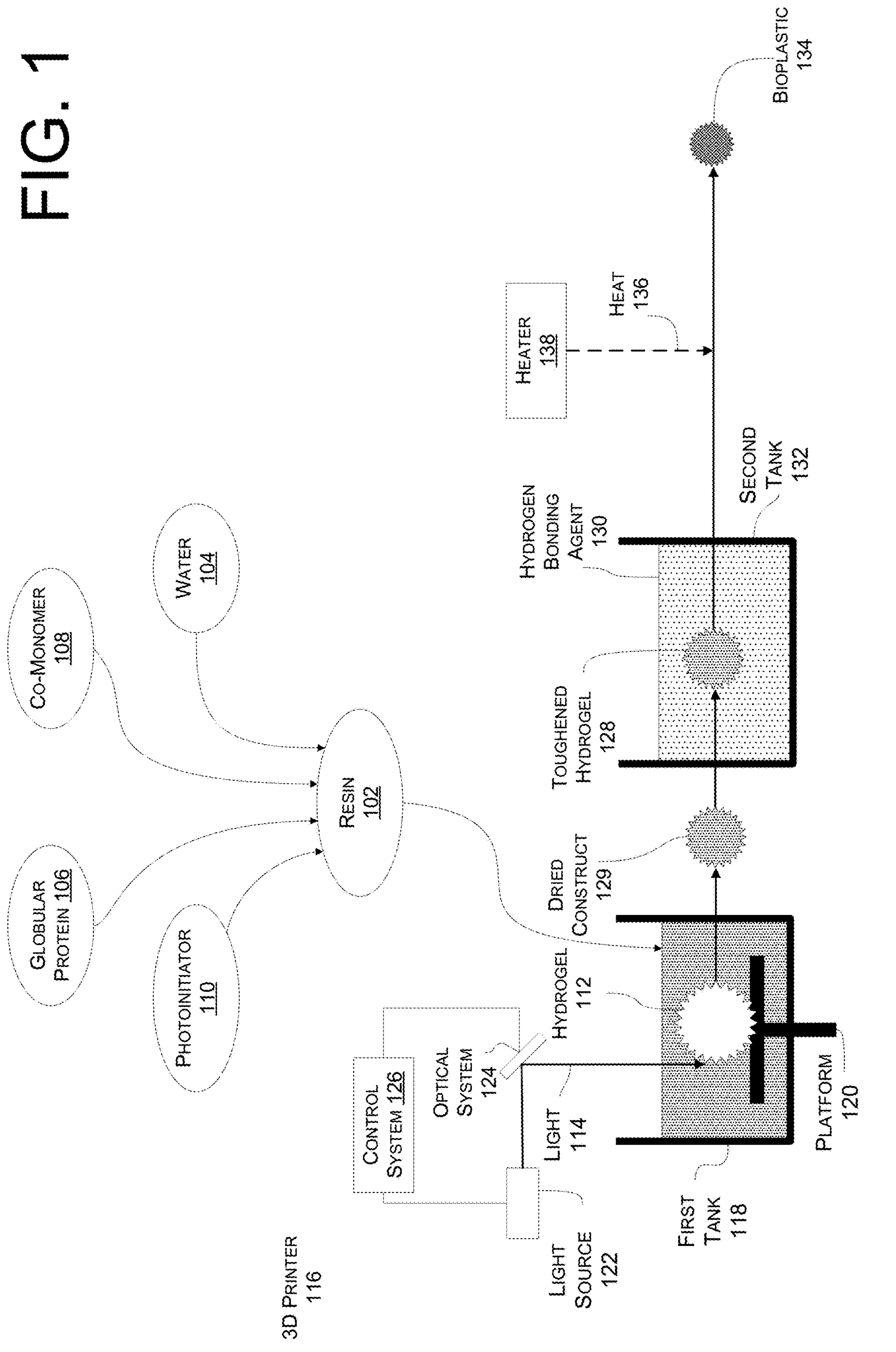
FIG. 1 illustrates an example environment for generating swelling-resistant materials.

FIG. 1 illustrates an example environment 100 for generating swelling-resistant materials. A resin 102 may be an aqueous solution that includes components configured to polymerize at a predetermined condition. In various implementations, the resin 102 includes various components, including water 104, a globular protein 106, and a co-monomer 108.

The globular protein 106 is soluble in the water 104. In various implementations, the globular protein 106 includes at least one polypeptide chain that is folded into a three-dimensional (3D) structure due to noncovalent interactions and disulfide bonds. In some cases, the globular protein 106 includes one or more methacrylate or acrylate groups. Examples of the globular protein 106 include a methacrylated enzyme, methacrylated legume protein, methacrylated lysozyme, methacrylated lactoglobulin, methacrylated hemoglobin, methacrylated pepsin, or methacrlyated serum albumin, acrylated enzyme, acrylated legume protein, acrylated lysozyme, acrylated lactoglobulin, acrylated hemoglobin, acrylated pepsin, or acrylated serum albumin. For instance, the globular protein 106 includes methacrylated bovine serum albumin (MABSA). In various implementations, the globular protein 106 is generated by exposing a non-methacrylated protein to a methacrylation reactant. For instance, the methacrylation reactant generates the one or more methacrylate groups in the globular protein 106 by causing the non-methacrylated protein to undergo an amidation reaction and/or Michael addition reaction. Examples of methacrylation reactants include methacrylic anhydride and methacryloyl chloride.

Michael addition reactions involve the nucleophilic addition of a nucleophile to an $\alpha,\beta$-unsaturated carbonyl compound containing an electron withdrawing group. Acrylated globular proteins are made using Michael addition reactions with compounds that have two or more acrylates. Examples of acrylation reactants include ethylene glycol diacrylate and polyethylene glycol diacrylate.

The co-monomer 108 is also soluble in water 104. In various cases, the co-monomer 108 includes an acrylate. For instance, the co-monomer 108 includes hydroxyethyl acrylate (HEA), acrylamide (AAm), polyethylene glycol diacrylate (PEG-DA), or a combination thereof. Other examples of acrylates include methacrylate, methyl acrylate, ethyl acrylate, acrylic anhydride, propargyl acrylate, allyl acrylate, polyethylene glycol monomethyl ether acrylate, butyl acrylate, and acrylic acid, 2-acrylamido-2-methylpropane sulfonic acid, and sodium 2-acrylamido methylpropane sulfonate. According to some examples, the amount of to co-monomer 108 in the resin 102 is minimized, to reduce degradation of constructs generated from the resin 102.

In addition, the resin 102 may include a photoinitiator 110. The photoinitiator 110, according to various implementations, is water soluble. The photoinitiator 110, for instance, induces radical photopolymerization and/or cationic photopolymerization of the globular protein 106 and the co-monomer 108 when activated. In some examples, the photoinitiator 110 includes an initiator and a co-initiator. According to various implementations, the photoinitiator 110 includes an alpha hydroxyketone or derivative (e.g., 2-hydroxy-1-[4-(2-hydroxyethoxy) phenyl]-2-methyl-1-propanone (Irgacure 2959), 1-hydroxy-cyclohexyl-phenylketone (Irgacure 184), 2-benzyl-2-dimethylamino-1-(4-morpholinophenyl)-1-butanone (Irgacure 369), 2-methyl-4'-(methylthio)-2-morpholinopropiophenone (Irgacure 907), 2-methyl-4'-(methylthio)-2-morpholinopropiophenone (Irgacure 907), or sodium 4-[2-(4-morpholino)benzoyl-2-dimethylamino] butylbenzenesulphone (MBS)), a phosphine derivative (e.g., diphenyl(2,4,6-trimethylbenzoyl) phosphine oxide (TPO) or lithium phenyl-2,4,6-trimethylbenzoylphosphinate (LAP)), an azo-initiator (e.g., 2,2'-azobis[2-methyl-N-(2-hydroxyethyl) promionamide] (VA-086)), eosin-Y and a co-initiator (e.g., an amine, such as triethanolamine or ethylamine), carboxylated camphorquinone and a co-initiator (e.g., an amine, such as triethylenamine and ethyl-4-N,N-dimethylaminobenzoate), riboflavin and a co-initiator (e.g., an amine, such as triethylamine), erythrosine and a co-initiator, or rose Bengal and a co-initiator. According to some cases, the photoinitiator 110 includes lithium phenyl-2,4,6-trimethylbenzoylphosphinate or 2-hydroxy-2-methylpropiophenone. In particular examples, the photoinitiator 110 is activated by light having a wavelength of 405 nanometers (nm) and includes a ruthenium complex (such as tris(2,2'-bipyridyl)dichlororuthenium(II) hexahydrate ($Ru(bpy)_3$) and a radical generator.

In various cases, the resin 102 may have various characteristics. For instance, the resin 102 may have a viscosity in a range of 0.25 Pas to 10 Pa·s. In addition, the resin 102 may have optical characteristics that enable the resin 102 to be transparent to a frequency of light that activates the photoinitiator 110. For instance, the resin 102 may transmit and/or photocure at an electromagnetic wavelength of 250-800 nm.

A hydrogel 112 may be generated by exposing the resin 102 to light 114. A frequency of the light 114 may depend on the photoinitiator 110 included in the resin 102. For example, the hydrogel 112 may be generated by loading the resin 102 in a photolithographic 3D printer 116. The 3D printer 116, for instance, includes a first tank 118 configured to hold the resin 102. A platform 120 is at least partially disposed in the first tank 118, and is configured to support the hydrogel 112 as it is generated in the first tank 118.

The 3D printer 116 further includes a light source 122 configured to emit the light 114, as well as an optical system 124 configured to direct, focus, and reflect the light 114 into the first tank 118. In various implementations, the light source 122 includes at least one laser. The optical system 114, for instance, includes one or more mirrors and/or one or more lenses. According to some examples, the optical system 114 further includes one or more actuators configured to reposition, turn, and otherwise move the mirrors and/or lenses. In various cases, a control system 126 is communicatively coupled to the light source 122 and the optical system 124. The control system 126 can be implemented by at least one processor and memory storing instructions that, when executed by the at least one processor, cause the at least one processor to perform various operations. In some cases, the control system 126 is implemented by a computing system. According to various examples, the control system 126 controls the operation of the light source 122 and/or optical system 124 in order to cause the light 114 to enter the first tank 118 in a particular pattern, thereby generating the hydrogel 112 in a predetermined 3D structure.

In various implementations, the light 114 activates the photoinitiator 110, thereby causing the globular protein 106 and co-monomer 108 to polymerize in the first tank 118. In various implementations, the co-monomer 108 binds to exposed methacrylated lysines in the globular protein 106. Further, methacrylated lysines of a first instance the globular protein 106 bind to methacrylated lysines of a second instance of the globular protein 106. Accordingly, the resin 102 is polymerized using the light 114.

In some examples, the hydrogel 112 is generated without the use of the 3D printer 116. For instance, the hydrogel 112 can be fabricated by filling a mold with the resin 102 and exposing the resin 102 to the light 114.

The hydrogel 112, in some cases, swells when it is exposed to water. That is, the hydrogel 112 may change size and/or shape based on its hydration status. In various implementations, the hydrogel 112 is converted into a toughened hydrogel 128, which may have different material characteristics than the hydrogel 112.

According to some examples, a dried construct 129 is generated by dehydrating the hydrogel 112, such as by exposing the hydrogel 112 to heat. The toughened hydrogel 128, in turn, may be generated by rehydrating the dried construct 129 with a solution including a hydrogen bonding agent 130.

As illustrated in FIG. 1, the hydrogen bonding agent 130 may be disposed in a second tank 132 and the toughened hydrogel 128 may be generated by placing the dried construct 129 in the second tank 132. Alternatively, the hydrogen bonding agent 130 could be disposed in the first tank 118 after the resin 102 has been removed, or could be deposited on the dried construct 129 using a sprayer.

The dried construct 129, if not exposed to the hydrogen bonding agent 130, would exhibit swelling and rehydration if exposed to water. In various implementations, the toughened hydrogel 128 is generated when the hydrogen bonding agent 130 diffuses into the dried construct 129. The hydrogen bonding agent 130, in various cases, is disposed between the crosslinked globular protein 106 and the co-monomer 108 in the toughened hydrogel 128. The hydrogen bonding agent 130 may be a polyphenol agent and/or polyphenolic compound. As used herein, the terms "polyphenolic agent," "polyphenolic compound," and their equivalents, may refer to a material including multiple phenol groups. Examples of the hydrogen bonding agent 130 include tannic acid, gallic acid, dopamine, or I-3,4-dihydroxyphenylalanine (L-DOPA). The hydrogen bonding agent 130 in the toughened hydrogel 128 may prevent the toughened hydrogel 128 from rehydrating. That is, the hydrogen bonding agent 130 prevents the toughened hydrogel 128 from swelling when the toughened hydrogel 128 is disposed in an aqueous environment. Furthermore, the toughened hydrogel 128 may have enhanced toughness compared to the hydrogel 112. The toughened hydrogel 128 may be defined as a composite of the hydrogel 112 and the hydrogen bonding agent 130. In examples in which the hydrogen bonding agent 130 is tannic acid, for instance, the toughened hydrogel 128 may be defined as a tannic acid-hydrogel composite.

In some cases, a bioplastic 134 is generated by exposing the toughened hydrogel 128 to heat 136. The heat 136, for instance, is generated by a heater 138. In various cases, the heat 136 raises the temperature of the toughened hydrogel 128 to a temperature above the denaturation temperature of the globular protein 106. Accordingly, the heat 136 may unfold the crosslinked globular protein 106 in the toughened hydrogel 128. The heat 136 treatment may denature the globular protein 106 and increase the hydrogen bond interconnectedness between the globular protein 106 and the co-monomer 108, thereby generating the bioplastic 134. The substantial hydrogen bonding between the denatured globular protein 106, the co-monomer 108, and the hydrogen bonding agent 130 within the bioplastic 134 enhances the toughness and physical properties of the bioplastic 134. For example, instances of the denatured globular protein 106 in the bioplastic 134, in various implementations, include alpha helices and/or beta sheets that participate in hydrogen bonding with the co-monomer 108 and/or other instances of the denatured globular protein 106 in the bioplastic 134.

The toughened hydrogel 128 and/or bioplastic 134 can be utilized for a variety of applications. For instance, the toughened hydrogel 128 and/or bioplastic 134 can be utilized in a synthetic graft, an implantable device, as a coating of an implantable device, in a surgical mesh, in a stent, in a patch, a bandage, or a microneedle structure. As used herein, the term "synthetic graft," and its equivalents, may refer to a man-made material used to replace or support a biological tissue. Examples of synthetic grafts include synthetic bone grafts (e.g., including calcium phosphate-based structures that can serve as scaffolds for which cells attach and generate new bone tissue), artificial skin (e.g., including a collagen scaffold that induces skingrowth), synthetic vascular grafts, synthetic intestinal mucosal grafts, and so on. In various implementations, the toughened hydrogel 128 and/or bioplastic 134 can be sutured to soft tissue, such as to skin, the abdominal wall, to blood vessel walls, a gastrointestinal (GI) tract, or the like. According to some cases, the toughened hydrogel 128 and/or bioplastic 134 degrades over time, such as when implanted in a subject.

In some implementations, the toughened hydrogel 128 and/or bioplastic 134 can include additional materials. According to some examples, a construct includes the toughened hydrogel 128 and/or bioplastic 134 as well as one or more additional materials, such as titanium, polyvinylchloride (PVC), polypropylene, polyethylene terephthalate (PET), polytetrafluorethylene (PTFE), polymethylmethacrylate (PMMA), stainless steel, silicone, or a ceramic. In some examples, the toughened hydrogel 218 and/or bioplastic 134 includes a therapeutic agent. Examples of the therapeutic agent include therapeutic proteins (e.g., antibody-based biologics, Fc fusion proteins, blood factors, growth factors, hormones, interleukins, etc.), antibiotics (e.g., cephalosporins, glycopeptides, lincomycins, macrolides, quinolones, sulfonamides, tetracyclines, etc.), and anti-inflammatory agents (e.g., corticosteroids, such as cortisone, prednisone, and methyl prednisolone; non-steroidal anti-inflammatory drugs (NSAIDs), such as aspirin and ibuprofen; anti tumor necrosis factor alpha (anti-TNF) biologics, such as adalimumab, certolizumibab pegol, etanercept, golimumab, and infliximab)). When the toughened hydrogel 218 and/or bioplastic 134 degrades over time (e.g., while being disposed inside the body of a subject), the therapeutic agent is released. In some examples, a construct including the toughened hydrogel 218 and/or bioplastic 134 includes engineered microbes that release a therapeutic agent. Accordingly, in various implementations, the toughened hydrogel 128 and/or bioplastic 134 can be utilized to deliver a therapeutic agent to a subject, such as when the construct is implanted into the subject.

In various implementations, a surface of a construct including the toughened hydrogel 128 and/or the bioplastic 134 is functionalized. For instance, the surface could be chemically modified and/or a material can be adsorbed to the surface. In various implementations, the surface is modified to fine-tune desired mechanical properties of the construct, to allow cells to adhere to the surface, to prevent cells from adhering to the surface, or to prevent diffusion of water or nutrients to other structures. In some cases, the surface is modified to enhance the biocompatibility of the construct.

Figure 2:
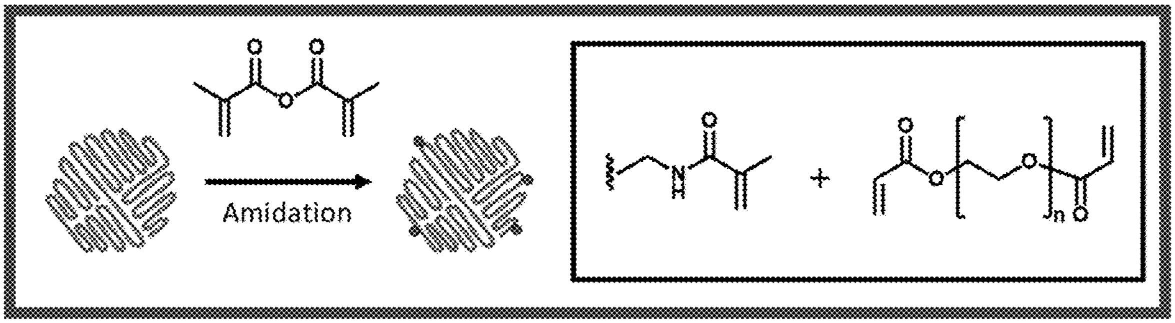
FIG. 2 illustrates an example of generating a methacrylated protein that can be included in a resin.

FIG. 2 illustrates an example of generating a methacrylated protein that can be included in a resin. For example, the process illustrated in FIG. 2 could be used to generate the globular protein 106 described above with reference to FIG. 1. In particular examples, the methacrylated protein is MABSA. In various implementations, the methacrylated protein is generated using a functionalization reactant, such as a methacrylation reactant (also referred to as a "methacrylation reagent" or "methacrylation agent"). For instance, the methcrylation reactant induces an amidation reaction on a non-methacrylated protein to generate a methacrylated protein. Alternatively, the methacrylated protein is generated when the methacrylation reactant induces a Michael addition reaction on the non-methacrylated protein. Examples of methacrylation reactants include methacrylic anhydride and methacryloyl chloride.

The non-methacrylated protein, for example, includes BSA, another type of serum albumin, pepsin, hemoglobin, lysozyme, lactoglobulin, a legume protein (e.g., soy protein), or an enzyme. As used herein, the term "legume protein," and its equivalents, can refer to a protein isolated from a legume. For example, legume proteins include globulin proteins, such as legumin and vicilin. Examples of soy protein include glycinin and beta-conglycynin. In various implementations, the methacrylated protein is generated by functionalizing available surface lysines of the non-methacrylated protein. In various implementations, 20-98% of the resin is the methacrylated protein, by weight (i.e., the resin is 20-98 wt % methacrylated protein).

Figure 3:
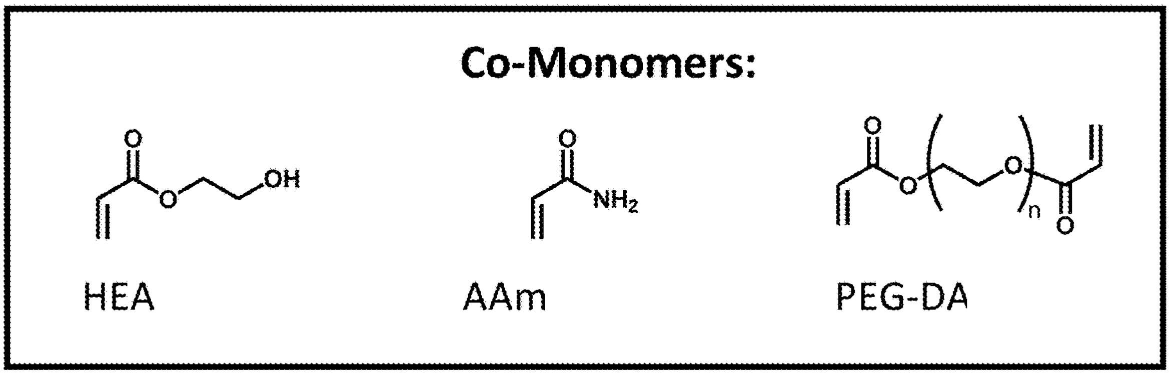
FIG. 3 illustrates example co-monomers that can be included in a resin.

FIG. 3 illustrates example co-monomers that can be included in a resin. For instance, one or more of the co-monomers illustrated in FIG. 3 could be used as the co-monomer 108 described above with reference to FIG. 1. The co-monomers illustrated in FIG. 3 include acrylate groups. Although three examples are illustrated in FIG. 3, implementations of the present disclosure include other acrylate-containing materials as co-monomers of the resin. The example co-monomers illustrated in FIG. 3 include, for instance, hydroxyethyl acrylate (HEA), acrylamide (AAm), and polyethylene glycol diacrylate (PEG-DA). Notably, the amount of the co-monomer in the resin is dependent on the type of co-monomer included. For instance, the resin incudes at least 3 wt % HEA, at least 2 wt % AAm, or at least 5 wt % PEG-DA.

Figure 4:
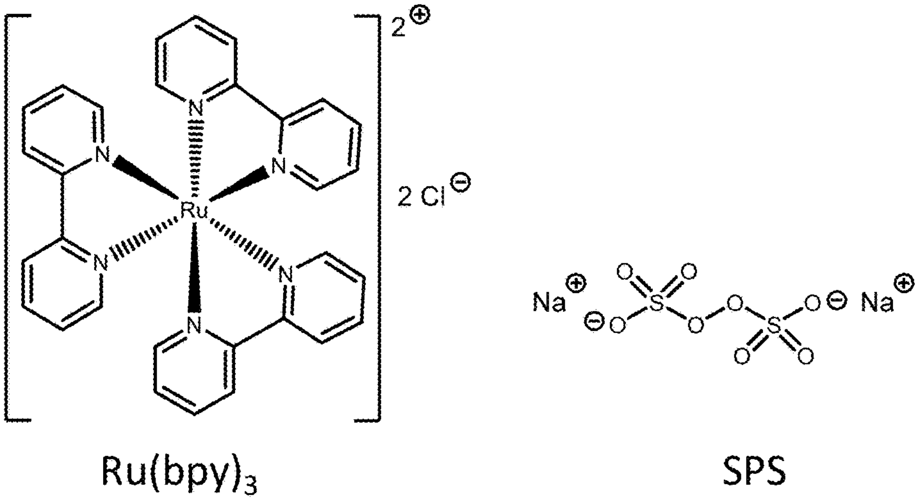
FIG. 4 illustrates an example photoinitiator that can be included in a resin.

FIG. 4 illustrates an example photoinitiator that can be included in a resin. The photoinitiator, for instance, includes a ruthenium complex and sodium persulfate (SPS). The ruthenium complex, for instance, is tris(2,2'-bipyridyl)dichlororuthenium(II) hexahydrate ($Ru(bpy)_3$). The photoinitiator illustrated in FIG. 4 may initiate crosslinking between a globular protein and a co-monomer when the resin is exposed to light at a wavelength of 250-800 nm. For example, the resin is polymerized by light having a wavelength of 405 nm.

Figure 5:
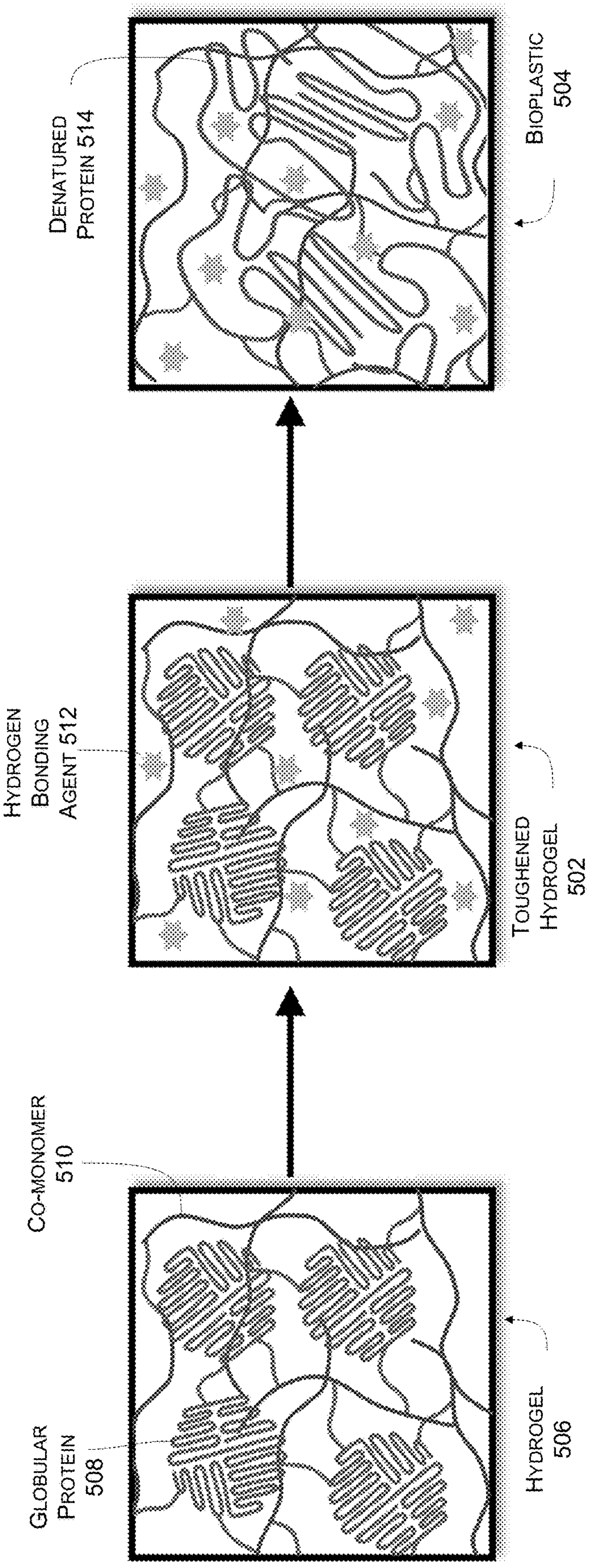
FIG. 5 illustrates an example process for generating a dried construct and a bioplastic from a hydrogel.

FIG. 5 illustrates an example process 500 for generating a toughened hydrogel 502 and a bioplastic 504 from a hydrogel 506. The hydrogel 506 includes a globular protein 508 that is cross-linked with a co-monomer 110. When the hydrogel 506 is dehydrated (e.g., heated) and rehydrated with a solution including a hydrogen bonding agent 512, the hydrogel 506 is transformed into the toughened hydrogel 502. The toughened hydrogel 502 includes the hydrogen bonding agent 512. In various examples, unlike the hydrogel 506, the toughened hydrogel 502 does not swell when exposed to water. If the toughened hydrogel 502 is exposed to a heat treatment, the globular protein 508 is denatured, thereby enabling new hydrogen bonds to form between neighboring globular proteins 508 and the co-monomer 510. The heat treatment transforms the toughened hydrogel 502 into the bioplastic 504, which includes the denatured form of the globular protein 508, otherwise referred to as a denatured protein 514. Like the toughened hydrogel 502, the bioplastic 504 does not swell when exposed to water.

Figure 6:
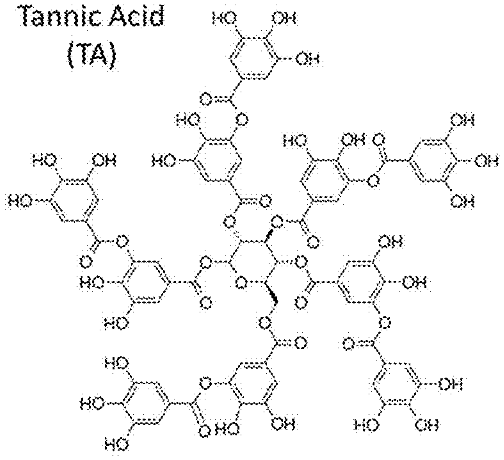
FIG. 6 illustrates tannic acid, which is an example hydrogen bonding agent.

FIG. 6 illustrates tannic acid, which is an example hydrogen bonding agent. Tannic acid, for instance, can be used to transform a hydrogel (e.g., hydrogel 112) into a toughened hydrogel (e.g., toughened hydrogel 128).

Figure 7A:
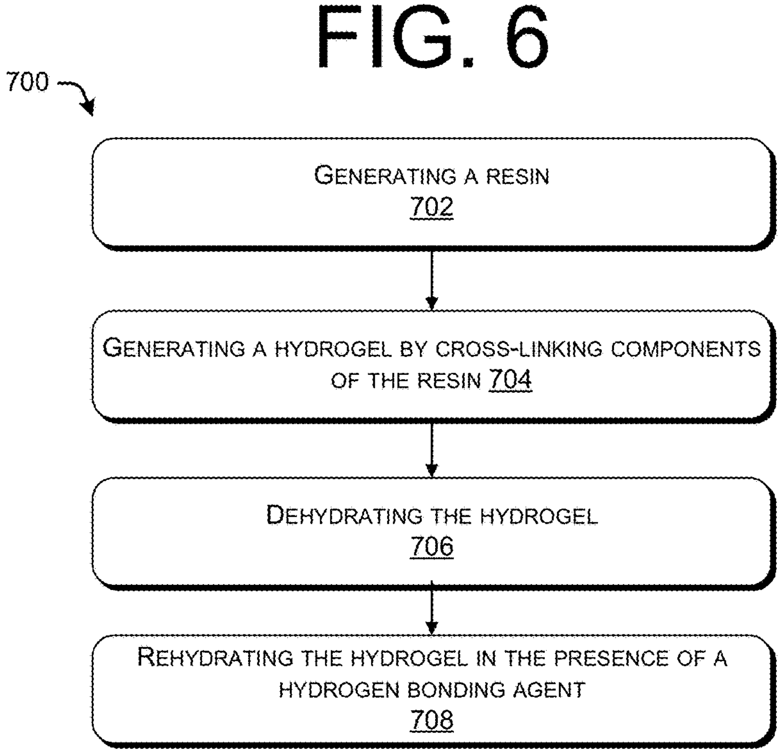
FIG. 7A illustrates an example process for generating a dried construct (also referred to as a "tough hydrogel").
Figure 7B:
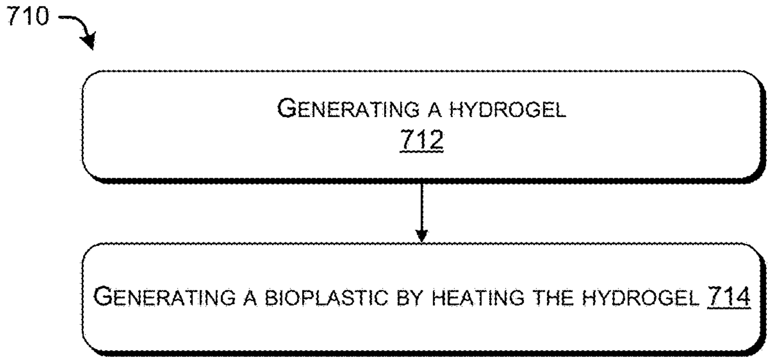
FIG. 7B illustrates an example process for generating a bioplastic.
Figure 8:
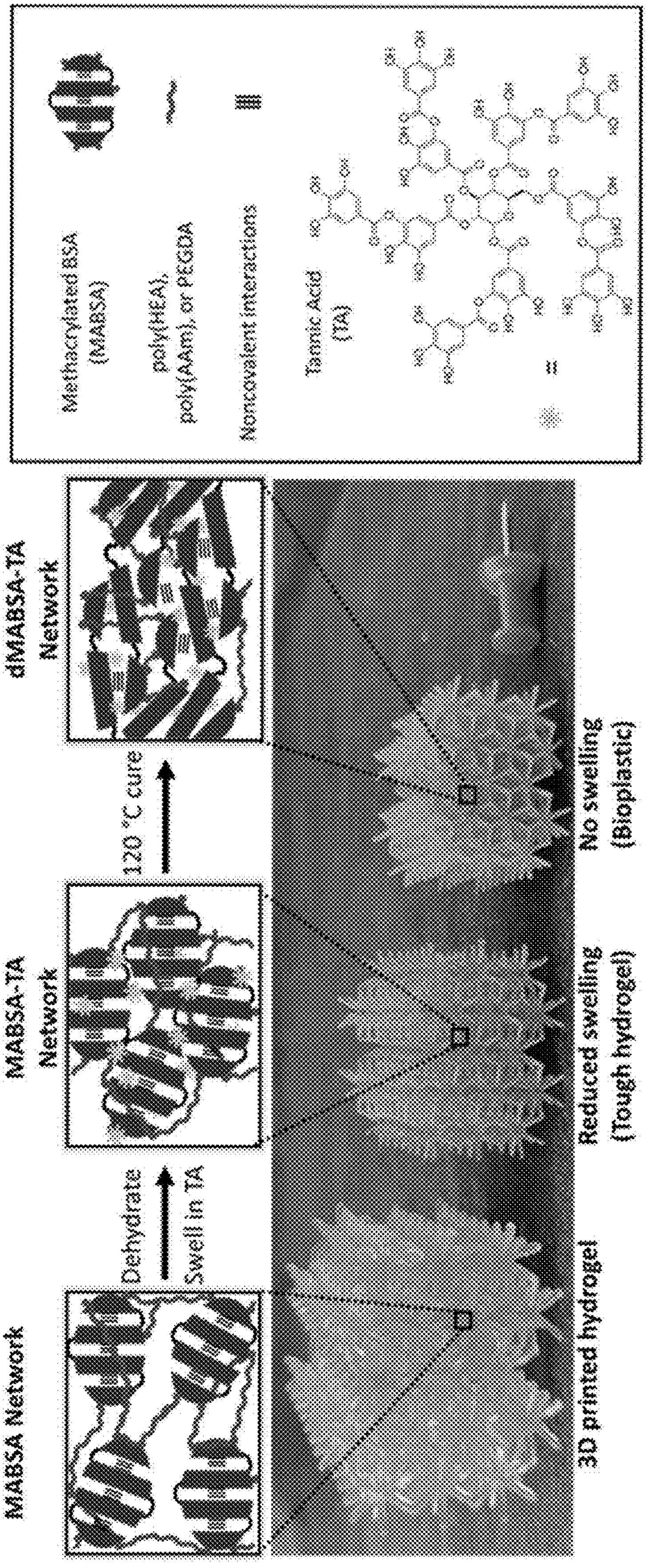
FIG. 8 illustrates a SLA 3D printed methacrylated bovine serum albumin (MABSA) lattice structure. Swelling in water of the as-printed hydrogels was controlled by incubation in a tannic acid (TA) solution. This TA treatment formed a tough MABSA-TA hydrogel. An additional 120°

FIGS. 7A and 7B illustrate example processes for generating constructs including non-swellable and biodegradable materials. The processes can be performed by an entity, such as a lab technician, a chemical plant, a microfluidic device, a processor, a 3D printer, or a combination thereof.

FIG. 7A illustrates an example process 700 for generating a toughened hydrogel (also referred to as a "tough hydrogel"). At 702, the entity generates a resin. In various implementations, the resin includes a globular protein. Examples of globular proteins include BSA, pepsin, and hemoglobin. In some instances, the globular protein is methacrylated. For example, the resin includes MABSA. In various cases, the methacrylated globular protein is generated by reacting one or more active sites of a non-methacrylated globular protein to a methacrylation reactant, thereby adding one or more methacryl groups to the globular protein. The methacrylation reactant initiates an amidation reaction or a Michael addition reaction.

In various implementations, the resin further includes a co-monomer. The co-monomer, in various cases, includes an acrylate. For instance, the co-monomer includes at least one ofPEGDA, HEA, AAm. Further, the resin includes a polymerization initiator. In various cases, the resin includes at least one photoinitiator, such as $Ru(bpy)_3$ and SPS. The resin, in various cases, is an aqueous solution. The various components of the resin are soluble in water, for instance.

At 704, the entity generates a hydrogel by cross-linking components of the resin. For instance, the entity activates the polymerization agent. In various implementations in which the resin includes a photoinitiator, the entity exposes the resin to light that activates the photoinitiator. The activated polymerization agent causes the globular protein to polymerize with the co-monomer. For instance, the methacrylation groups on the methacrylated globular protein react with the acrylate in the co-monomer. Further, the methacrylation groups of one methacrylated globular protein also link to methacrylation groups of neighboring methacrylated globular proteins. As a result of the polymerization, the resin is converted into a hydrogel.

At 706, the entity dehydrates the hydrogel. In some implementations, the entity exposes the hydrogel to heat, thereby removing water from the hydrogel. In some cases, the entity dehydrates the hydrogel at a temperature of 20-30° C. (e.g., 23° C.). At 708, the entity rehydrates the hydrogel in the presence of a hydrogen bonding agent. In various implementations, the hydrogen bonding agent is a polyphenol agent. For instance, the hydrogen bonding agent includes TA. The hydrogen bonding agent, in various cases, is included in an aqueous solution. The hydrogel is exposed to the hydrogen bonding agent by immersing the hydrogel in the aqueous solution and/or spraying the hydrogel with the hydrogen bonding agent.

The hydrogel is converted into a tough hydrogel after being exposed to the hydrogen bonding agent at 708. For example, the tough hydrogel is resistant to swelling if subsequently immersed in water or another aqueous solution. In various cases, the tough hydrogel is suturable.

FIG. 7B illustrates an example process 710 for generating a bioplastic. At 712, the entity generates a hydrogel. For example, the entity may perform the process 700 described above with reference to FIG. 7A.

At 714, the entity generates the bioplastic by heating the hydrogel. In various implementations, the heat causes a protein structure in the hydrogel (e.g., a globular protein cross-linked with a co-monomer and other instances of the globular protein in the hydrogel) to denature. The denatured protein structure induces different hydrogen bonds than those present in the hydrogel. As a result of these different hydrogen bonds, the bioplastic is generated. The bioplastic, in various implementations, has enhanced toughness when compared to the hydrogel generated at 712.

Experimental Examples

Particular examples of hydrogels and bioplastics will now be described. In some examples, MABSA-based resin formulations for 3D printing were utilized to generate printed constructs that only partially degraded in the presence of protease and became mechanically weaker upon swelling in water (P. T. Smith, B. Narupai, J. H. Tsui, S. C. Millik, R. T. Shafranek, D.-H. Kim, A. Nelson, Biomacromolecules 2020, 21). In various implementations of the present disclosure, alternative hydrogels were generated that exhibited minimal protease degradation and minimal to no swelling in water.

In various cases, utilization of PEGDA as a non-degradable reactive co-monomer (10 wt % of the resin) in the MABSA-based resin formulations limited the ability of protease to digest the protein network, as the construct only degraded 22% in a concentrated solution of proteinase K. Further, the utilization of the nondegradable PEGDA network limited the access of the enzyme to the protein matrix. In particular, replacing PEGDA with monofunctional co-monomers to form linear chains affords 3D matrices that can be fully degraded.

However, in some cases, the MABSA/PEGDA-based networks exhibited swelling in water. Addition of TA as an additive to the printed constructs yielded hydrogels and bioplastics that retained their toughness even in the presence of water.

In particular cases, three co-monomers were utilized as additives to MABSA-based resin formulations: AAm, HEA, and PEGDA. For instance, the resin formulations can include 30 wt % MABSA, with 0.075 wt % $Ru(bpy)_3Cl_2$ and 0.24 wt % SPS as the photoinitiating system. The minimum quantity of co-monomer additive required to produce a printable resin was determined by printing cylinders using a Form 2 printer with 1-10 wt % of co-monomer. Resin formulations with <3 wt % AAm, <2 wt % HEA, or <5 wt % PEGDA exhibited insufficient photocuring rates, which resulted in delamination between layers and failed prints. At equal or greater values than these respective concentrations of co-monomer, the MABSA resin exhibited formation of hydrogels and bioplastics.

In some examples, post-print processing of the printed constructs with TA was shown to increase toughness of the materials of the printed construct. Treatment of the printed constructs can include immersing the printed constructs in a solution of 300 mg/mL TA for 72 h to infuse TA into the polymer matrix to generate MABSA-TA composite hydrogels. In particular, incorporation of noncovalent interactions (primarily hydrogen bonding) between MABSA and TA was shown to improve the toughness of these materials by providing a mechanism for energy dissipation. FTIR spectra of the MABSA-TA network hydrogel showed that the peak representing TA carbonyl groups shifted from 1700 to 1721 $cm^{-1}$, confirming the formation of hydrogen bonds between TA and the printed MABSA structures (FIG. 16). Gravimetric analysis of the samples showed that the masses of the dehydrated TA composites were higher than those before TA infusion and contained up to 25 wt % TA relative to the total dry mass (Table 7).

In some examples, the influence of TA on the swelling behavior of the printed constructs was shown to be modified via different treatments including TA treatment, 120° C. thermal cure, and the combination of the two treatments (TA and 120° C. thermal cure). After the TA treatment, the swelling ratio of the MABSA-AAm, MABSA-HEA, and MABSA-PEGDA hydrogels reduced by more than 50% for each formulation (FIG. 9). Thermal treatment of photocured MABSA has been shown to result in loss of α-helix structure with concomitant formation of intermolecular β-sheets (E. Sanchez-Rexach, P. T. Smith, A. Gomez-Lopez, M. Fernandez, A. L. Cortajarena, H. Sardon, A. Nelson, ACS Appl. Mater. Interfaces 2021, 13, 19193). Separately, the thermal treatment and TA treatment each decreased the swelling ratio of the printed constructs in water by roughly the same amount. Notably, a combination of TA treatment followed by 120° C. thermal treatment greatly reduced the swelling ratio to below 0.11 for all formulations (FIG. 9).

Figure 10A:
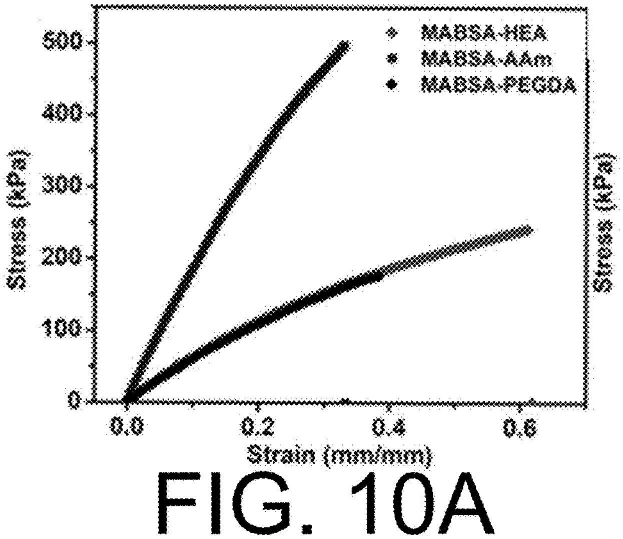
Figure 10B:
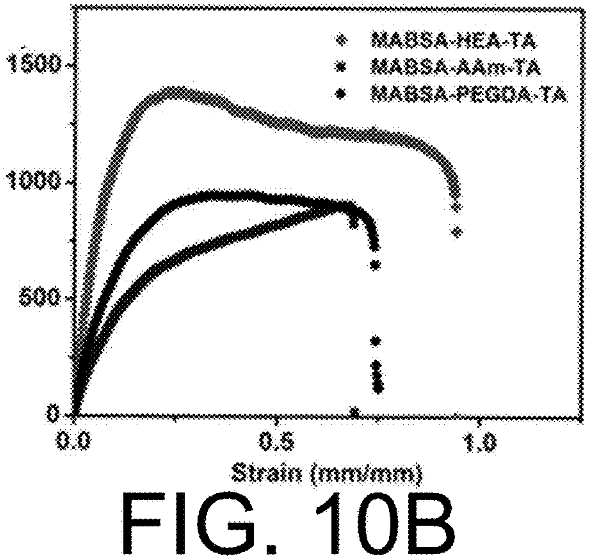
Figure 10C:
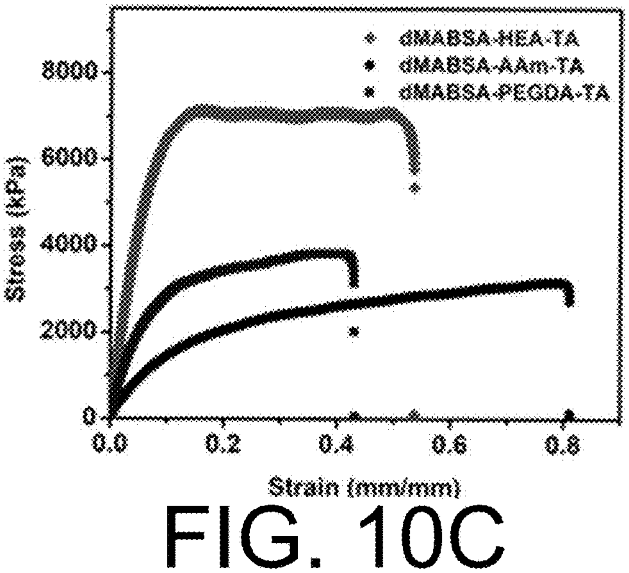
Figure 10D:
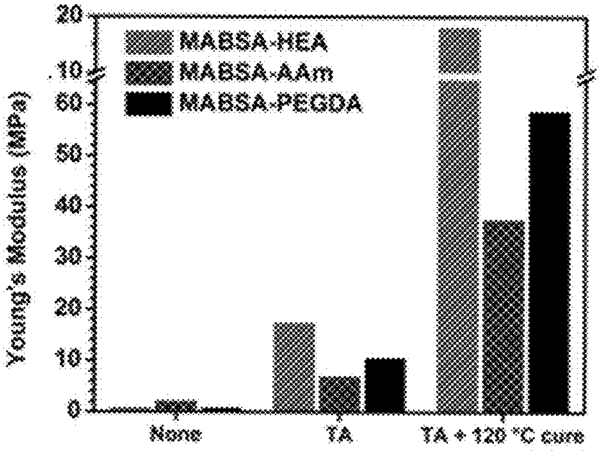
Figure 10E:
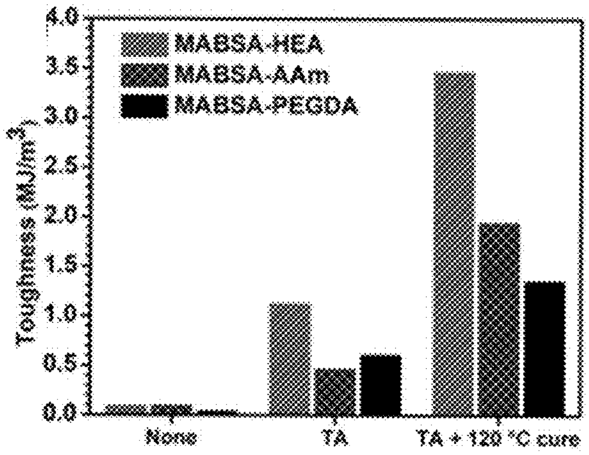
Figure 10F:
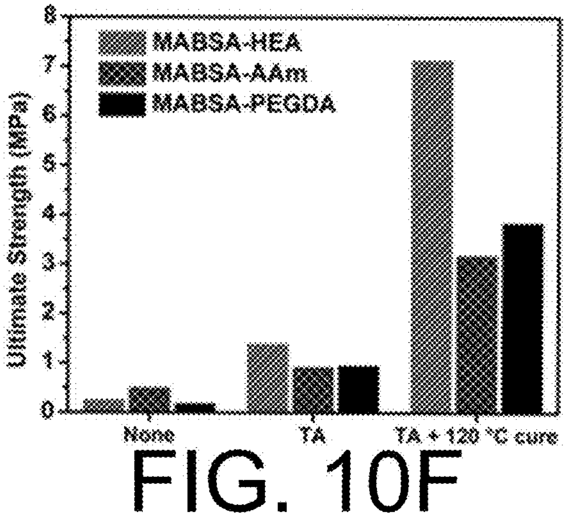
Figure 10J:
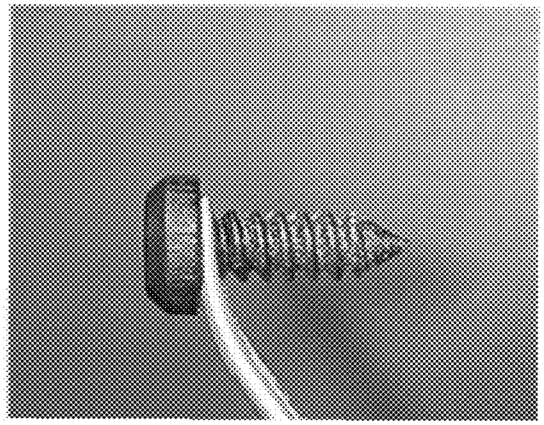
Figure 10I:
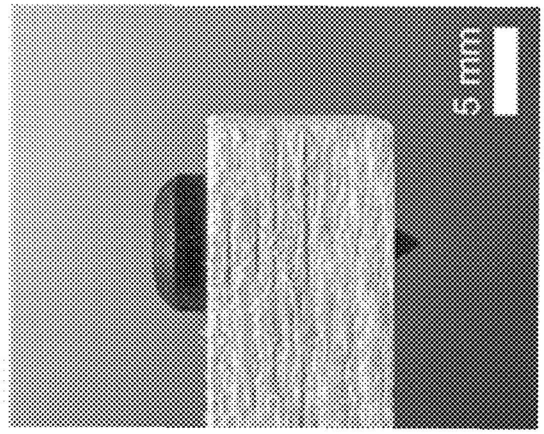

In some examples, the uniaxial tensile mechanical properties of the cured materials (ultimate strength, toughness, and elastic modulus) were studied using a load frame (FIG. 10A-10F). Among the non-treated hydrogels, MABSA-AAm had the highest Young's modulus (2.02 MPa), which was 3 times those of MABSA-HEA (0.64 MPa) and MABSA-PEGDA (0.68 MPa) (FIG. 10D). Similarly, MABSA-AAm demonstrated the highest ultimate strength and toughness (FIGS. 10E & 10F). These results are likely due to the additional hydrogen bonding interactions between the acrylamide groups and MABSA. The TA treatment afforded higher ultimate strength and toughness for all formulations. When compared to the non-treated samples, the ultimate strength increased 27-fold for MABSA-HEA-TA, 3.4-fold for MABSA-AAm-TA, and 15-fold for MABSA-PEGDA-TA. These improvements may be attributed to energy dissipation afforded by the disruption of hydrogen bonding and other noncovalent interactions (M. A. Gonzalez, J. R. Simon, A. Ghoorchian, Z. Scholl, S. Lin, M. Rubinstein, P. Marszalek, A. Chilkoti, G. P. Lopez, X. Zhao, Adv. Mater. 2017, 29, 1; J. Fang, A. Mehlich, N. Koga, J. Huang, R. Koga, X. Gao, C. Hu, C. Jin, M. Rief, J. Kast, D. Baker, H. Li, Nat. Commun. 2013, 4; L. Zhao, X. Zhang, Q. Luo, C. Hou, J. Xu, J. Liu, Biomacromolecules 2020, 21, 4212; and M. A. Da Silva, S. Lenton, M. Hughes, D. J. Brockwell, L. Dougan, Biomacromolecules 2017, 18, 636). The increased hydrogen bonding interactions that are introduced with the presence of TA in the matrix decreased the water uptake by the composite materials and also improved the mechanical properties of the swollen hydrogels. Finally, the samples that were thermally cured at 120° C. after the TA treatment exhibited the greatest improvements in mechanical properties. The ultimate strength increased to 7.1 MPa for dMABSA-HEA-TA, 3.2 MPa for dMABSA-AAm-TA, and 3.8 MPa for dMABSA-PEGDA-TA. These increases in mechanical strength were also accompanied by significant reductions in water uptake. Thus, the post-print TA treatment followed by thermal cure transforms the as-printed hydrogels into bioplastic materials (which show minimal rehydration in water).

Figure 10H:
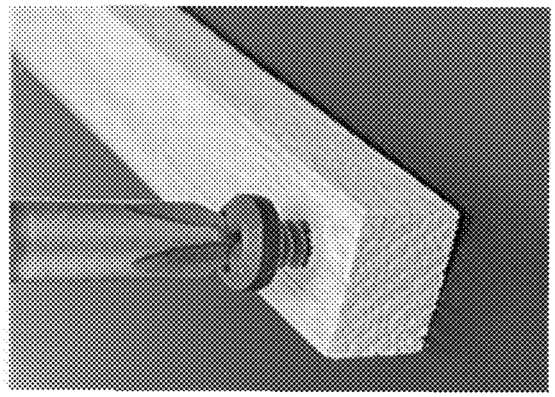
Figure 10G:
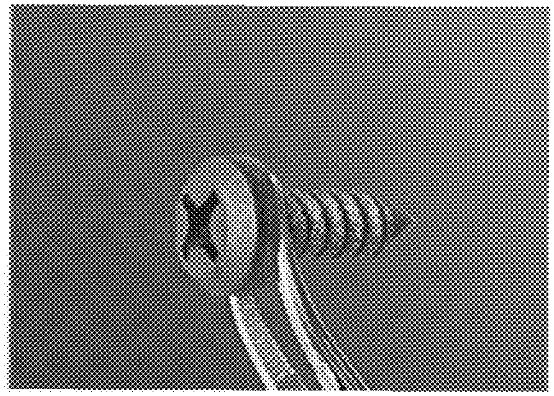
Figure 11A:
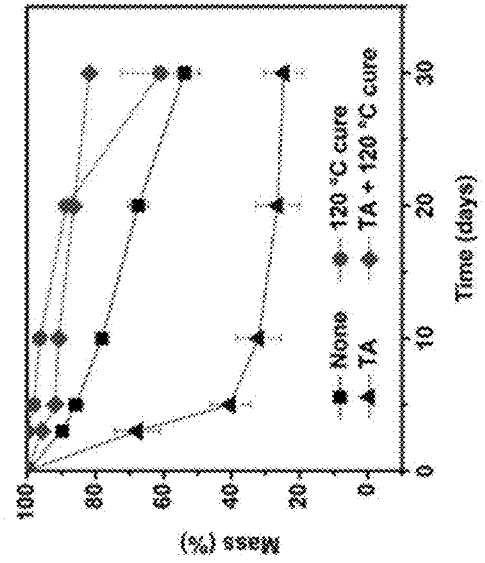
Figure 11B:
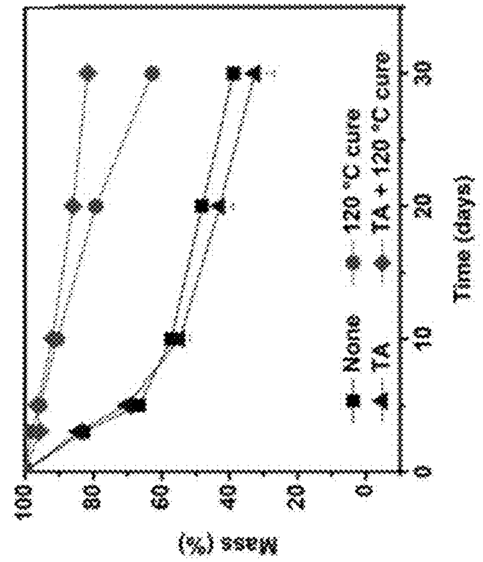
Figure 11C:
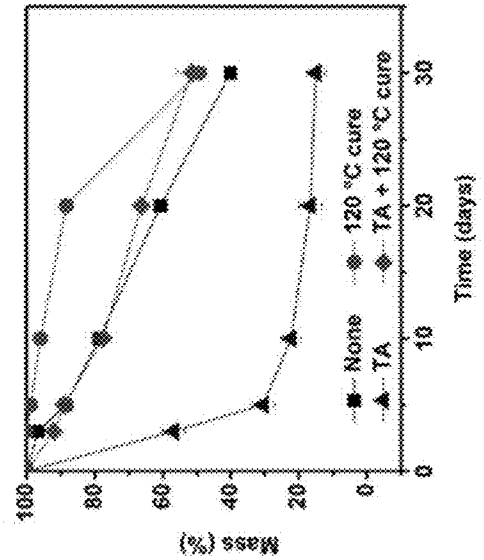
Figure 11D:
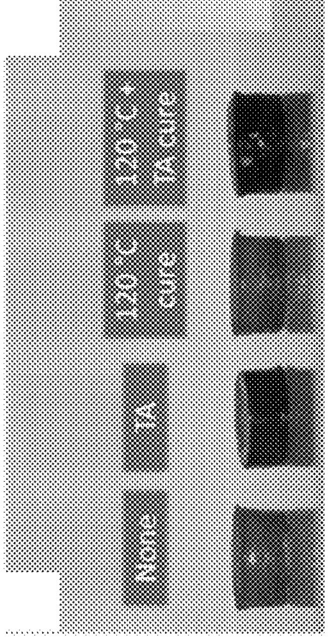
Figure 11E:
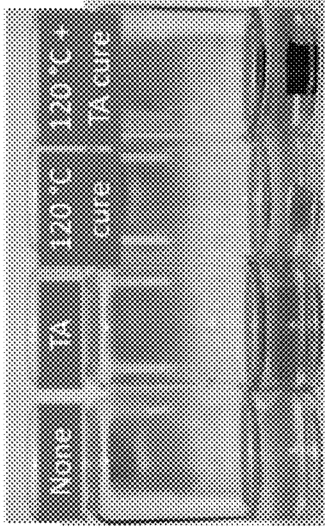
Figure 11F:
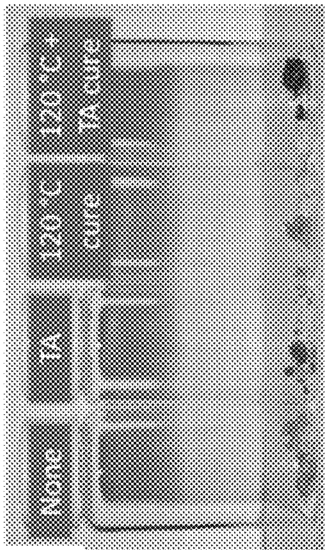

In some examples, the bioplastics exhibited high mechanical strength in various 3D printed forms. For example, a mechanically functional screw was fabricated and driven into a piece of balsa wood. The MABSA-AAm resin was formulated with 0.075 wt % New Coccine (a red food dye) to enhance the resolution of the printed features (M. D. Castilho, J. Malda, R. Levato, C. R. Alcala-Orozco, F. P. W. Melchels, D. Gawlitta, G. J. Hooper, T. B. F. Woodfield, P. F. Costa, K. S. Lim, K. M. A. van Dorenmalen, Biofabrication 2018, 10, 034101). The screw was successfully driven into a piece of balsa wood and then removed without any visible signs of structural damage to the screw (FIG. 10H).

In some examples, the resins can be utilized to generate hydrogels and bioplastics that exhibit biodegradable qualities with degradation rates that depended upon the material composition and post-print processing conditions. In particular, the biodegradability of these materials was investigated over the course of 30 days in a pepsin solution (pH 1.5-2.0). Without any post-print treatment, the samples degraded 46.0%, 61.2%, and 59.9% for MABSA-HEA, MABSA-AAm, and MABSA-PEGDA, respectively (FIG. 11). Regardless of co-monomer used, the samples with TA treatment exhibited the greatest mass loss, 75.3% for MABSA-HEA-TA, 67.5% for MABSA-AAm-TA, and 85.0% for MABSA-PEGDA-TA. This increase in degradation could be the result of TA disrupting protein interactions and providing greater access to enzymes (R. Osawa, T. Walsh, J. Agric. Food Chem 1993, 41, 704). Additionally, polyphenols have been shown to enhance the enzymatic activity of pepsin (D. Tagliazucchi, E. Verzelloni, A. Conte, J. Agric. Food Chem. 2005, 53, 8706). Samples that were treated with TA and 120° C. exhibited the lowest degradation rates. Accordingly, the hydrogels and the bioplastics can be tailored via material composition and treatments to modulate the amount of degradation experienced by the hydrogels and the bioplastics.

Figure 12A:
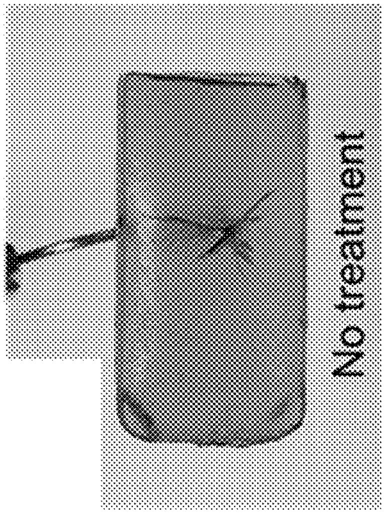
Figure 12B:
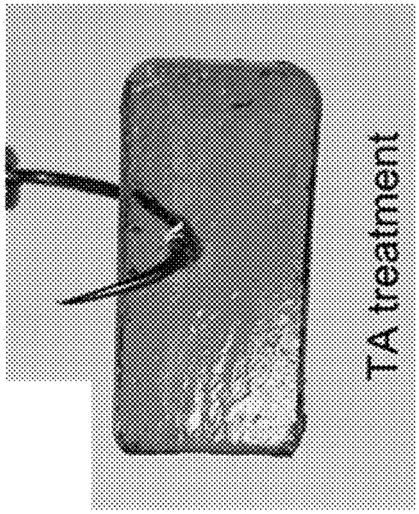
Figure 12C:
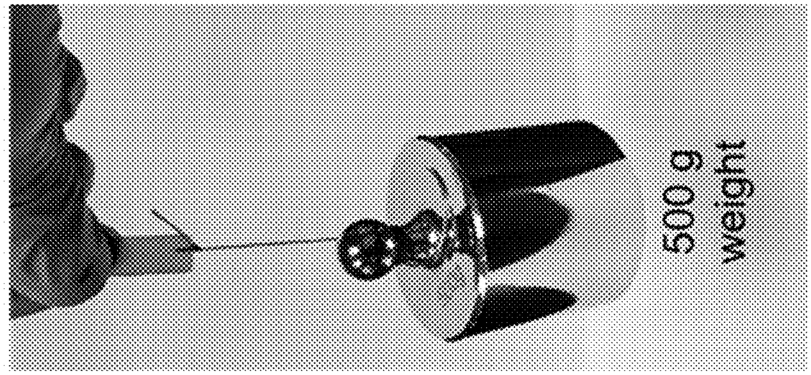
Figure 12D:
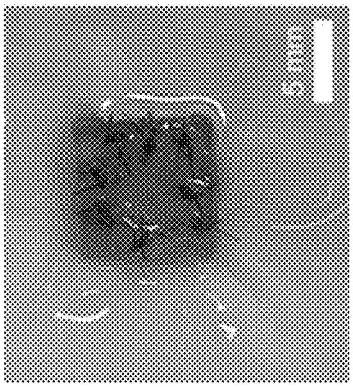
Figure 12E:
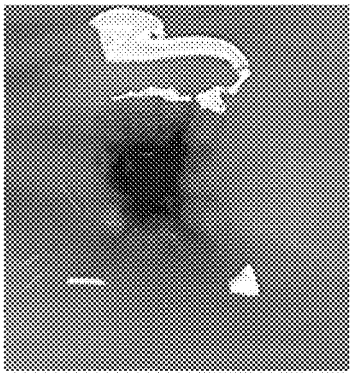
Figure 12F:
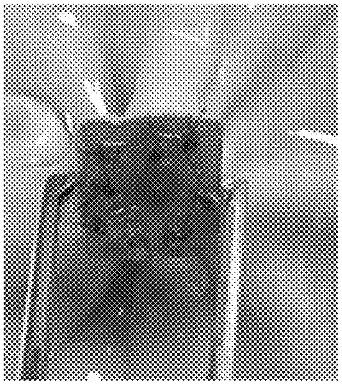
Figure 12G:
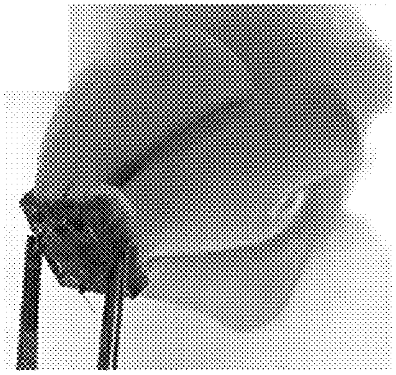

In some examples, the hydrogel and/or the bioplastic generated from the MABSA resin can exhibit improved mechanical functionality. In particular, the MABSA-based hydrogels (or bioplastics) were tested to determine the mechanical functionality for additional applications. Accordingly, the response of the hydrogels and/or bioplastics to suturing (FIG. 12A to 12G) was utilized to determine the capabilities of the MABSA-based hydrogels in response to TA treatment, thermal curing, and combinations of the two treatments. The MABSA-based hydrogels without post-print treatments were brittle and exhibited crack propagation throughout the material upon suture insertion, as shown in FIG. 12A. Additionally, after TA treatment, a 3 mm thick sample exhibited markedly reduced crack propagation (FIG. 12B) and could support 500 g loaded on a single loop of suture material (FIG. 12C). To demonstrate suturing to tissue, a hydrogel patch (8 mm×8 mm) was 3D printed and treated with TA. A square of matching size was cut from a section of bovine small intestine, and after equilibration in water, the hydrogel patch was sutured in place. The sutures held firmly even after 24 h of water immersion (FIGS. 12F and 12G).

In summary, an additive manufacturing process can be utilized to generate hydrogels and bioplastics from MABSA, or other globular proteins analog, and TA, or other hydrogen bonding compound. The fabricated protein-based hydrogels and bioplastics can be generated as 3D printed constructs that exhibited excellent mechanical properties (modulus, strength, and toughness) and can biodegrade in the presence of proteases. A mechanically functional screw was 3D printed to showcase the utility afforded to bioplastic constructs by this process. The broad range of mechanical properties achievable with this material platform coupled with the ability to support suturing suggests opportunities for the design of 3D printable and degradable for applications in sustainable bioplastics and biomedical devices.

Experiments were performed utilizing materials including methacrylic anhydride (94%), Tris(2,2'-bipyridyl)dichlororuthenium(II) hexahydrate (Ru(bpy)3Cl2) (99.95%), poly(ethylene glycol) diacrylate (Mn 700 Da), poly(ethylene glycol) methyl ether acrylate (Mn 480 Da), tannic acid, 2-hydroxyethyl acrylate, acrylamide, sodium persulfate (SPS), and New Coccine (75% dye content) that were used as received. Additionally, low fatty acid content BSA was obtained to be utilized in creation of the MABSA.

Methacrylation of BSA was accomplished by adding BSA (20 g, 0.3 mmol) and $NaHCO_3/Na_2CO_3$ buffer (200 mL, 0.25 M, pH 9.0) were to a 1000 mL round-bottom flask equipped with a magnetic stir bar. The mixture was stirred at 2-8° C. until the BSA dissolved completely. Then, methacrylic anhydride (4 mL, 27 mmol, 2.5 eq. per lysine residue) was added dropwise to the BSA solution over 10 min. The reaction mixture was stirred at 2-8° C. for 2 hr. The crude product was diluted two-fold with deionized (DI) water and then dialyzed against DI water for 48 h at 2-8° C. After dialysis, the product was lyophilized with yields typically >91.5%. The percent functionalization of the available lysines of BSA with methacryloyl functionalities was determined using a 2,4,6-trinitrobenzene sulfonate (TNBS) assay (P. T. Smith, B. Narupai, J. H. Tsui, S. C. Millik, R. T. Shafranek, D.-H. Kim, A. Nelson, Biomacromolecules 2020, 21).

All resin formulations were prepared in amber bottles and covered with aluminum foil to prevent auto-polymerization. Three resin formulations were generated for testing, each of the resin formulations including 30 wt % MABSA and an amount of a co-monomer that generates a printable resin: 5 wt % for poly(ethylene glycol) diacrylate (PEGDA), 3 wt % for acrylamide (AAm), and 2 wt % for 2-hydroxyethyl acrylate (HEA). The weight percentages are based on the total composition of the resin, including DI water as the solvent. As a representative example, 6 g of the resin includes 30 wt % MABSA and 5 wt % PEGDA. First, 0.3 g of PEGDA was dissolved in 3.66 mL of DI water; then, 1.8 g of MABSA was slowly added to this solution with gentle mixing until dissolved. Finally, 0.075 wt % $Ru(bpy)_3Cl_2$ was dissolved in 120 μL of DI water, and 0.24 wt % SPS was dissolved in 120 μL of DI water; these solutions were sequentially added to the resin formulation with gentle mixing. The final resin formulation was covered with aluminum foil and stored at 4° C. until use. To prepare the other formulations, similar procedures were followed, changing only the co-monomer and DI water quantity. For fabrication of the bioplastic screw, 0.075 wt % New Coccine was included in the resin formulation. The screw thread geometry was difficult to resolve without inclusion of a photoabsorber (M. D. Castilho, J. Malda, R. Levato, C. R. Alcala-Orozco, F. P. W. Melchels, D. Gawlitta, G. J. Hooper, T. B. F. Woodfield, P. F. Costa, K. S. Lim, K. M. A. van Dorenmalen, Biofabrication 2018, 10, 034101 and J. Field, J. W. Haycock, F. M. Boissonade, F. Claeyssens, Molecules 2021, 26).

SLA 3D printing of MABSA-based hydrogels was accomplished by utilizing a commercial 3D printer with a modified build platform and resin tray was to fabricate one or more hydrogel constructs (P. T. Smith, B. Narupai, J. H. Tsui, S. C. Millik, R. T. Shafranek, D.-H. Kim, A. Nelson, Biomacromolecules 2020, 21). Hydrogel constructs were printed with the commercial 3D printer to include a layer height of 100 μm. Upon completion of the print, samples were removed from the build platform, rinsed in DI water to remove uncured resin, and post-cured in a photocuring chamber (Quans, 400 nm, 1 mW/cm2) for 90 min. Some samples were further treated with TA, thermally cured at 120° C., or treated with both TA and heating.

TABLE 1

Photorheological properties of 30 wt % MABSA resin formulations.

| Additive | Gel point (s) | G' @ 30 s (kPa) |
|---|---|---|
| 1 wt % HEA | 9.7 | 73.4 |
| 2 wt % HEA | 7.6 | 273.1 |
| 2 wt % AAm | 6.5 | 513.5 |
| 3 wt % AAm | 5.8 | 420.1 |
| 4 wt % PEGDA | 11.8 | 113.2 |
| 5 wt % PEGDA | 9.5 | 132.8 |

TA solutions for treatment of the MABSA hydrogels were prepared by dissolving TA in DI water at a concentration of 300 mg/mL, with pure DI water included as a control. For the TA treatment, 3D printed MABSA hydrogel constructs were photocured, dehydrated, then immersed in TA solution for 72 h, to produce tough TA-MABSA hydrogel constructs. Free TA was removed by equilibration in DI water. Some samples were then thermally cured at 120° C. to produce virtually non-rehydratable bioplastics.

Thermal curing of the MABSA hydrogels with or without TA treatment was performed after photocuring the hydrogel constructs. After photocuring of the hydrogel constructs, and optionally after the TA treatment, the hydrogel constructions were dehydrated and placed in a 120° C. oven for 180 min.

TA content of the MABSA hydrogel can be determined from 3D printed MABSA hydrogel disks (10 mm diameter, 5 mm height). In particular, the MABSA hydrogen disks can be equilibrated in DI water for 24 h to remove unreacted MABSA and co-monomer. Then, the disks can be vacuum dried and weighed ($m_i$). After immersing the disks in 300 mg/mL TA solution for 72 h, unbound TA was removed by equilibration in DI water for 24 hr. Finally, the disks were vacuum dried and weighed ($m_f$). The TA content was calculated as follows:

$$TA\text{ content }(\%) = \left(\frac{m_f - m_i}{m_i}\right) \times 100 \quad \text{Equation 1}$$

TABLE 2

Remaining concentration of TA remaining in printed constructs after equilibration in DI water

| Formulation | TA concentration (wt %) |
|---|---|
| 2 wt % HEA | 25.4 |
| 3 wt % AAm | 16.6 |
| 5 wt % PEGDA | 7.9 |

TABLE 3

Effect of TA concentration on swelling ratio

| TA concentration | Swelling ratio 24 h TA incubation | Swelling ratio 72 h TA incubation | Swelling ratio 72 h TA incubation + 120° C. cure |
|---|---|---|---|
| 0 mg/mL | 2.37 | 2.32 | 0.81 |
| 50 mg/mL | 1.84 | 1.58 | 0.45 |
| 100 mg/mL | 1.30 | 0.90 | 0.42 |
| 150 mg/mL | 1.21 | 0.73 | 0.33 |
| 200 mg/mL | 0.98 | 0.61 | 0.33 |
| 250 mg/mL | 0.93 | 0.58 | 0.26 |
| 300 mg/mL | 0.92 | 0.58 | 0.17 |

3D printed MABSA hydrogel disks (10 mm diameter, 5 mm height) were subjected to post-print treatments (either 120° C. thermal cure, TA treatment, 120° C. thermal cure and TA treatment, or no treatment). Disks were then vacuum dried and measured in height and diameter to determine volume ($V_i$). The disks were then equilibrated in DI water for 24 h and measured in diameter and height to determine volume ($V_f$). The swelling ratio was calculated as follows:

$$\text{Swelling ratio} = \left(\frac{V_f - V_i}{V_i}\right) \quad \text{Equation 2}$$

Compression tests were performed using a load frame with a 2 kN load cell. 3D printed MABSA hydrogel disks (10 mm diameter, 5 mm height) were 3D printed as described above. Hydrogel disks were tested at equilibrium swelling with DI water. All tests were conducted at room temperature (22° C.) using a crosshead rate of 1.3 mm/min until specimen failure or 80% strain. Prior to testing, the hydrated specimens were removed from DI water, blotted dry, and measured to determine the dimensions of the hydrated specimens via a digital caliper. At least 5 specimens of each formulation (MABSA-AAm, MABSA-HEA, and MABSA-PEGDA) and post-print treatment (120° C. thermal cure, TA treatment, 120° C. thermal cure and TA treatment, or no treatment) were tested. Compressive modulus and strength were calculated from the resulting stress-strain curves.

TABLE 4

Compression data for MABSA-HEA

| Post print treatment | E (MPa) | σ (MPa) | ε (mm/mm) | Toughness (MJ/m3) |
|---|---|---|---|---|
| DI | 3.0 | 0.74 | 0.28 | 0.10 ± 0.01 |
| 120° C. cure | 6.3 | 6.0 | 0.49 | 1.13 ± 0.06 |
| TA | 6.6 | 12.0 | 0.76 | 2.07 ± 0.26 |
| TA + 120° C. cure | 48.8 | 286.0 | 0.70 | 50.20 ± 3.34 |

TABLE 5

| Compression data for MABSA-PEGDA | | | | |
|---|---|---|---|---|
| Post print treatment | E (MPa) | σ (MPa) | ε (mm/mm) | Toughness (MJ/m3) |
| DI | 2.2 | 1.0 | 0.40 | 0.16 ± 0.02 |
| 120° C. cure | 4.5 | 5.2 | 0.50 | 1.14 ± 0.13 |
| TA | 4.5 | 9.7 | 0.72 | 1.55 ± 0.26 |
| TA + 120° C. cure | 35.4 | 173.0 | 0.70 | 31.10 ± 2.50 |

TABLE 6

| Compression data for MABSA-AAm | | | | |
|---|---|---|---|---|
| Post print treatment | E (MPa) | σ (MPa) | ε (mm/mm) | Toughness (MJ/m3) |
| DI | 8.1 | 1.8 | 0.27 | 0.23 ± 0.04 |
| 120° C. cure | 5.5 | 5.3 | 0.45 | 1.04 ± 0.05 |
| TA | 5.1 | 15.4 | 0.65 | 3.25 ± 0.14 |
| TA + 120° C. cure | 30.2 | 215.0 | 0.70 | 39.27 ± 2.09 |

Tensile mechanical measurements were performed by utilizing a 1 kN load cell to determine the tensile performance of the MABSA hydrogels and bioplastics. ASTM D638 type V specimens were printed and post-print treated as described above. Specimens were tested at equilibrium swelling with DI water. All tests were conducted at room temperature (22° C.) using a crosshead rate of 5 mm/min until specimen failure. Prior to testing, the hydrated specimens were removed from DI water, blotted dry, and measured to determine the dimensions of the specimens were via a digital caliper. At least 5 specimens of each formulation (MABSA-AAm, MABSA-HEA, and MABSA-PEGDA) and post-print treatment (120° C. thermal cure, TA treatment, 120° C. thermal cure and TA treatment, or no treatment) were tested. Tensile modulus, tensile strength, and tensile toughness values were calculated from the resulting stress-strain curves. Toughness was calculated as the area under the stress-strain curve; this was done using a MATLAB program. Compressive modulus was determined from the slope of the elastic region of the stress-strain curve.

TABLE 7

| Tensile data for MABSA-HEA | | | | |
|---|---|---|---|---|
| Post print treatment | E (MPa) | σ (MPa) | ε (mm/mm) | Toughness (kJ/m3) |
| None | 0.64 | 0.24 | 0.61 | 89.66 |
| TA | 17.26 | 1.38 | 0.94 | 1120.80 |
| TA + 120° C. cure | 118.00 | 7.12 | 0.54 | 3461.5 |

TABLE 8

| Tensile data for MABSA-PEGDA | | | | |
|---|---|---|---|---|
| Post print treatment | E (MPa) | σ (MPa) | ε (mm/mm) | Toughness (kJ/m3) |
| None | 0.68 | 0.18 | 0.39 | 39.18 |
| TA | 10.5 | 0.95 | 0.75 | 608.61 |
| TA + 120° C. cure | 58.7 | 3.84 | 0.43 | 1354.60 |

TABLE 9

| Tensile data for MABSA-AAm | | | | |
|---|---|---|---|---|
| Post print treatment | E (MPa) | σ (MPa) | ε (mm/mm) | Toughness (kJ/m3) |
| None | 2.02 | 0.50 | 0.33 | 93.32 |
| TA | 6.81 | 0.91 | 0.67 | 464.16 |
| TA + 120° C. cure | 37.4 | 3.17 | 0.81 | 1940.30 |

Biodegradation behaviors of 3D printed constructs were characterized by incubation in pepsin solution. Biodegradation assays were performed at 37° C. in a shaking incubator at 221 rpm. The incubation medium was prepared by dissolving pepsin (>2500 U/mg) at 3.2 g/L in 0.1 M HCl (pH 1.5-2.0). DI water and a solution of 0.1 M HCl (pH 1.5-2.0) were used as controls. 4 mL of incubation medium was added to each test structure. Dry mass data were collected on days 3, 5, 10, 20 and 30. Dry mass for each sample was measured after drying the sample under vacuum. The percentage of remaining dry mass was calculated as follows:

Equation 3

$$\%\ \text{remaining dry mass} = \frac{(\text{Dry mass after biodegradation})}{\text{Initial dry mass}} \times 100$$

TABLE 10

| Data from "Additive manufacturing of bovine serum albumin-based hydrogels and bioplastics" | | |
|---|---|---|
| Day | % mass loss (control) | % mass loss (Proteinase K) |
| 0 | — | — |
| 1 | 2.8 | 9.6 |
| 2 | 2.0 | 11.7 |
| 7 | 4.5 | 22.0 |

Example Clauses

1. A method for generating a construct, the method including: generating a resin including about 10 to 40% methacrylated bovine serum albumin (MABSA) by weight, about 2 to 10% a water soluble co-monomer by weight, water, and a photoinitiator; generating a hydrogel by exposing the resin to light, thereby polymerizing the MABSA and the co-monomer; generating a dried construct by removing at least a portion of the water from the hydrogel; generating a tannic-acid-hydrogel composite by submerging the dried construct in an aqueous solution including tannic acid; and generating a bioplastic by heating the tannic acid-hydrogel composite at a temperature of about 100 to 130° Celsius (C), wherein generating the bioplastic includes dehydrating the tannic acid-hydrogel composite.
2. The method of clause 1, wherein the resin includes about 30% MABSA by weight and 2 to 4% the water soluble co-monomer by weight, and wherein the tannic acid-hydrogel composite is heated at the temperature of about 120° C.
3. The method of clause 1 or 2, wherein the water soluble co-monomer includes at least one of poly(ethylene glycol) diacrylate (PEGDA), hydroxyethylacrylate (HEA), or acrylamide (AAm).

4. A bioplastic, including: a denatured globular protein including one or more methacrylated lysines that are exposed on an outer surface of the denatured globular protein; a co-monomer crosslinking the denatured globular protein with one or more additional denatured globular proteins, the co-monomer being bound with a methacrylated lysine of the one or more methacrylated lysines and an additional methacrylated lysine of the one or more additional denatured globular proteins; and a hydrogen bonding agent crosslinking the denatured globular protein with the one or more additional denatured globular proteins.
5. The bioplastic of clause 4, wherein the denatured globular protein includes at least one of denatured pepsin, denatured hemoglobin, denatured lysozyme, denatured lactoglobulin, denatured soy protein, or denatured serum albumin.
6. The bioplastic of clause 4 or 5, wherein the denatured globular protein includes one or more alpha helices and/or one or more beta sheets that are formed during a heat-curing process.
7. The bioplastic of any one of clauses 4 to 6, wherein the co-monomer includes at least one of poly(ethylene glycol) diacrylate (PEGDA), hydroxyethylacrylate (HEA), or acrylamide (AAm).
8. The bioplastic of any one of clauses 4 to 7, wherein the bioplastic includes a coating of an implantable device.
9. A surgical mesh or implantable device including the bioplastic of any one of clauses 4 to 8.
10. A synthetic graft including the bioplastic of any one of clauses 4 to 8.
11. A method, including: generating a resin including a globular protein having one or more active sites, a co-monomer, water, and a photoinitiator; generating a hydrogel by exposing the resin to light, thereby polymerizing the globular protein and the co-monomer; dehydrating the hydrogel by removing at least a portion of the water; and rehydrating the hydrogel in the presence of a hydrogen bonding agent.
12. The method of clause 11, wherein the globular protein includes at least one of pepsin, hemoglobin, or serum albumin.
13. The method of clause 11 or 12, wherein the co-monomer includes at least one of poly(ethylene glycol) diacrylate (PEGDA), hydroxyethylacrylate (HEA), or acrylamide (AAm).
14. The method of any one of clauses 11 to 13, wherein generating the hydrogel by exposing the resin to light includes: providing the resin in a tank; and generating the hydrogel by irradiating the resin in the tank with the light, the hydrogel including a three-dimensional (3D) structure.
15. The method of any one of clauses 11 to 14, wherein the photoinitiator includes: tris(2,2'-bipyridyl)dichlororuthenium(II) hexahydrate ($Ru(bpy)_3$) and sodium persulfate (SPS); lithium phenyl-2,4,6-trimethylbenzoylphosphinate; or 2-hydroxy-2-methylpropiophenone.
16. The method of any one of clauses 11 to 15, wherein the hydrogen bonding agent includes a polyphenolic compound.
17. The method of any one of clauses 11 to 16, further including: reacting one or more of the active sites of the globular protein with a functionalization reactant, wherein generating the resin is in response to reacting the one or more active sites of the globular protein with the functionalization reactant.
18. The method of clause 17, wherein the functionalization reactant is a methacrylation reactant that reacts with the one or more active sites of the globular protein to add one or more methacrylate groups to the globular protein.
19. The method of any one of clauses 11 to 18, further including: in response to rehydrating the hydrogel in the presence of the hydrogen bonding agent, generating a bioplastic by heating the hydrogel.
20. The bioplastic generated using the method of clause 19.
21. A method including: receiving an amount of a globular protein in an aqueous solution; receiving a functionalization reactant that reacts with one or more active sites associated with the globular protein to convert the globular protein into a reactive protein; receiving, an additional amount of a water-soluble comonomer to the aqueous solution; initiating photopolymerization of the activated protein and the additional amount of the water-soluble comonomer to generate a hydrogel construct; and treating the hydrogel construct with a hydrogen bonding agent to convert the hydrogel construct into a toughened construct.
22. The method of clause 21, wherein the globular protein is at least one of pepsin, hemoglobin, soy, pea, or albumin protein.
23. The method of clause 21 or 22, wherein the functionalization reactant is a methacrylation reactant that reacts with the one or more active sites on the globular protein to add one or more methacryl groups to the globular protein thereby forming the activated protein.
24. The method of clause 23, wherein the one or more active sites are one or more lysines within the globular protein.
25. The method of any one of clauses 21 to 24, wherein the water-soluble comonomer is at least one of poly (ethylene glycol) diacrylate (PEGDA), hydroxyethylacrylate (HEA), or acrylamide (AAm).
26. The method of any one of clauses 21 to 25, wherein initiating photopolymerization includes: providing the aqueous solution that includes the activated protein and the additional amount of the water-soluble comonomer to a photopolymerization vat; and causing a light source to activate and initiate polymerization of the activated protein and the water-soluble comonomer to form the hydrogel construct.
27. The method of clause 26, wherein the light source causes the water-soluble comonomer to cross link the activated protein via the one or more active sites.
28. The method of any one of clauses 21 to 27, wherein the hydrogen bonding agent is tannic acid.
29. The method of any one of clauses 21 to 28, wherein treating the hydrogel construct with the hydrogen bonding agent includes: removing the hydrogel construct from the aqueous solution; dehydrating the hydrogel construct; and placing the hydrogel construct into a container that contains the hydrogen bonding agent.
30. The method of clause 29, wherein: placing the hydrogel construct into the container of the hydrogen bonding agent causes the hydrogel construct to absorb the hydrogen bonding agent; and the hydrogen bonding agent reacts with the activated protein within the hydrogel construct to form one or more crosslinks, converting the hydrogel construct into the toughened construct.
31. The method of any one of clauses 21 to 30, wherein the water-soluble comonomer cross-links a first activated protein with one or more additional activated proteins; and the water-soluble comonomer causes the hydrogel to be included of at least one of linear biopolymer that include substantially linear chains of the activated protein and the water-soluble comonomer or biopolymer networks that include the first activated protein bonded to the one or more additional activated proteins via the water-soluble comonomer.

32. The method of any one of clauses 21 to 31, further including curing the toughened construct at a cure temperature associated with the globular protein to convert the toughened construct into a bioplastic construct.
33. The method of clause 32, wherein the cure temperature exceeds a denaturing temperature of the globular protein and causes the activated protein within the toughened construct to denature.
34. The method of clause 32 or 33, further including: applying a degradation agent to the bioplastic construct; and causing the degradation agent to break down the bioplastic construct such that a structure of the bioplastic construct is removed.
35. The method of clause 34, wherein the degradation agent is a protease that breaks down the activated protein within the bioplastic construct.
36. The method of any one of clauses 21 to 35, further including: applying a degradation agent to the toughened construct; and causing the degradation agent to break down the toughened construct such that a structure of the toughened construct is removed.
37. The method of clause 36, wherein the degradation agent is a protease that breaks down the activated protein within the toughened construct.
38. A hydrogel including: a globular protein that includes one or more methacrylated lysines that are exposed on an outer surface of the globular protein; a comonomer that crosslinks the globular protein with one or more additional globular proteins, the comonomer reacting with a methacrylated lysine of the one or more methacrylated lysines and an additional methacrylated lysine of the one or more additional globular proteins; and a hydrogen bonding agent that crosslinks the globular protein with the one or more additional globular proteins, wherein the globular protein, the one or more additional globular proteins, and the comonomer form a biopolymer that is crosslinked by the hydrogen bonding agent.
39. The hydrogel of clause 38, wherein the globular protein is at least one of pepsin, hemoglobin, or serum albumin.
40. The hydrogel of clause 38 or 39, wherein the comonomer is at least one of poly(ethylene glycol) diacrylate (PEGDA), hydroxyethylacrylate (HEA), or acrylamide (AAm).
41. The hydrogel of any one of clauses 38 to 40, wherein the hydrogen bonding agent is tannic acid.
42. The hydrogel of any one of clauses 38 to 41, wherein the globular protein includes one or more alpha helices.
43. The hydrogel of any one of clauses 38 to 42, wherein the globular protein includes one or more beta sheets that are formed from one or more alpha helices during a curing process of the hydrogel.

CONCLUSION

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms “include” or “including” should be interpreted to recite: “comprise, consist of, or consist essentially of.” The transition term “comprise” or “comprises” means has, but is not limited to, and allows for the inclusion of unspecified elements, steps, ingredients, or components, even in major amounts. The transitional phrase “consisting of” excludes any element, step, ingredient or component not specified. The transition phrase “consisting essentially of” limits the scope of the implementation to the specified elements, steps, ingredients or components and to those that do not materially affect the implementation. As used herein, the term “based on” is equivalent to “based at least partly on,” unless otherwise specified.

Unless otherwise indicated, all numbers expressing quantities, properties, conditions, and so forth used in the specification and claims are to be understood as being modified in all instances by the term “about.” Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term “about” has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms “a,” “an,” “the” and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gin), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like. As indicated elsewhere, variants of gene sequences can include codon optimized variants, sequence polymorphisms, splice variants, and/or mutations that do not affect the function of an encoded product to a statistically-significant degree.

Variants of the protein sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

Certain implementations are described herein, including the best mode known to the inventors for carrying out implementations of the disclosure. Of course, variations on these described implementations will become apparent to those of ordinary skill in the art upon reading the foregoing description. The inventor expects skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

What is claimed is:

1. A method, comprising:

generating a resin comprising a co-monomer, water, a photoinitiator, and a globular protein having one or more active sites;

generating a hydrogel by exposing the resin to light, thereby polymerizing the globular protein and the co-monomer;

dehydrating the hydrogel by removing at least a portion of the water; and rehydrating the hydrogel in the presence of a hydrogen bonding agent, the hydrogen bonding agent comprising a polyphenolic compound.

2. The method of claim 1, wherein the globular protein comprises at least one of pepsin, hemoglobin, or serum albumin.

3. The method of claim 1, wherein the co-monomer comprises at least one of poly(ethylene glycol) diacrylate (PEGDA), hydroxyethylacrylate (HEA), or acrylamide (AAm).

4. The method of claim 1, wherein generating the hydrogel by exposing the resin to light comprises:

providing the resin in a tank; and generating the hydrogel by irradiating the resin in the tank with the light, the hydrogel comprising a three-dimensional (3D) structure.

5. The method of claim 1, wherein the photoinitiator comprises:

tris(2,2'-bipyridyl) dichlororuthenium (II) hexahydrate ($Ru(bpy)_3$) and sodium persulfate (SPS);

lithium phenyl-2,4,6-trimethylbenzoylphosphinate; or 2-hydroxy-2-methylpropiophenone.

6. The method of claim 1, further comprising:

reacting one or more of the active sites of the globular protein with a functionalization reactant, wherein generating the resin is in response to reacting the one or more active sites of the globular protein with the functionalization reactant.

7. The method of claim 6, wherein the functionalization reactant is a methacrylation reactant that reacts with the one or more active sites of the globular protein to add one or more methacrylate groups to the globular protein.

8. The method of claim 1, further comprising:

in response to rehydrating the hydrogel in the presence of the hydrogen bonding agent, generating a bioplastic by heating the hydrogel.

9. A bioplastic generated using the method of claim 8.

10. A surgical mesh comprising the bioplastic of claim 9.

11. An implantable device comprising the bioplastic of claim 9.

12. A synthetic graft comprising the bioplastic of claim 9.

13. The bioplastic of claim 9, further comprising a therapeutic agent.

14. The bioplastic of claim 13, wherein the therapeutic agent comprises a therapeutic protein, an antibiotic, an anti-inflammatory agent, or an anti tumor necrosis factor alpha (anti-TNF) biologic.

15. The method of claim 1, wherein the globular protein comprises a methacrylated enzyme, a methacrylated legume protein, a methacrylated lysozyme, a methacrylated lactoglobulin, a methacrylated hemoglobin, a methacrylated pepsin, a methacrylated serum albumin, an acrylated enzyme, an acrylated legume protein, an acrylated lysozyme, an acrylated lactoglobulin, an acrylated hemoglobin, an acrylated pepsin, or an acrylated serum albumin.

16. The method of claim 1, wherein the co-monomer is water-soluble.

17. The method of claim 1, wherein the hydrogen bonding agent comprises at least one of tannic acid, gallic acid, dopamine, or L-3,4-dihydroxyphenylalanine (L-DOPA).

18. The method of claim 1, further comprising:

generating the globular protein by methacrylating at least one of a serum albumin, pepsin, hemoglobin, lysozyme, lactoglobulin, legumin, vicilin, glycinin, beta-conglycynin, or an enzyme.

19. A method, comprising:

generating a resin comprising a co-monomer, water, a photoinitiator, and a globular protein having one or more active sites;

generating a hydrogel by exposing the resin to light, thereby polymerizing the globular protein and the co-monomer;

dehydrating the hydrogel by removing at least a portion of the water;

rehydrating the hydrogel in the presence of a hydrogen bonding agent; and in response to rehydrating the hydrogel in the presence of the hydrogen bonding agent, generating a bioplastic by heating the hydrogel.

* * * * *